United States Patent
Ning et al.

(10) Patent No.: US 12,414,751 B2
(45) Date of Patent: Sep. 16, 2025

(54) ERGONOMIC IMPROVEMENTS IN CONE BEAM BREAST COMPUTED TOMOGRAPHY

(71) Applicant: Koning Corporation, Norcross, GA (US)

(72) Inventors: Ruola Ning, Atlanta, GA (US); Shaohua Liu, Atlanta, GA (US)

(73) Assignee: Koning Corporation, Norcross, GA (US)

( * ) Notice: Subject to any disclaimer, the term of this patent is extended or adjusted under 35 U.S.C. 154(b) by 0 days.

(21) Appl. No.: 18/914,208

(22) Filed: Oct. 13, 2024

(65) Prior Publication Data

US 2025/0032060 A1    Jan. 30, 2025

Related U.S. Application Data

(63) Continuation of application No. PCT/US2023/018359, filed on Apr. 12, 2023.

(60) Provisional application No. 63/430,571, filed on Dec. 6, 2022, provisional application No. 63/401,546, filed on Aug. 26, 2022, provisional application No. 63/401,513, filed on Aug. 26, 2022, provisional application No. 63/401,475, filed on Aug. 26, 2022, provisional application No. 63/401,548, filed on Aug. 26, 2022, provisional application No. 63/401,493, filed on Aug. 26, 2022, provisional application No. 63/331,153, filed on Apr. 14, 2022.

(51) Int. Cl.
| | | |
|---|---|---|
| A61B 6/00 | (2024.01) | |
| A61B 6/03 | (2006.01) | |
| A61B 6/04 | (2006.01) | |
| A61B 6/40 | (2024.01) | |
| A61B 6/50 | (2024.01) | |
| A61B 8/08 | (2006.01) | |
| G06T 7/00 | (2017.01) | |

(52) U.S. Cl.
CPC .............. *A61B 6/502* (2013.01); *A61B 6/032* (2013.01); *A61B 6/035* (2013.01); *A61B 6/0435* (2013.01); *A61B 6/0478* (2013.01); *A61B 6/0487* (2020.08); *A61B 6/4085* (2013.01); *A61B 8/0825* (2013.01); *G06T 7/00* (2013.01); *G06T 2207/30068* (2013.01)

(58) Field of Classification Search
CPC ............................... A61B 6/502; A61B 6/032
See application file for complete search history.

(56) References Cited

U.S. PATENT DOCUMENTS

| | | |
|---|---|---|
| 3,640,520 A | 2/1972 | Wieland et al. |
| 4,650,172 A | 3/1987 | Wathelet |
| 6,504,892 B1 | 1/2003 | Ning |

(Continued)

OTHER PUBLICATIONS

Crotty et al., Investigating Novel Patient Bed Designs for Use in a Hybrid Dual Modality Dedicated 3D Breast Imaging System; Medical Imaging 2007: Physics of Medical Imaging, edited by Jiang Hsieh, Michael J. Flynn, Proc. of SPIE vol. 6510, 65101H, (2007).

*Primary Examiner* — Dani Fox
(74) *Attorney, Agent, or Firm* — Bergman LLC; Michael Bergman

(57) ABSTRACT

A cone beam breast computed tomography system includes a pivotable patient interface panel such that a patient can be introduced to the panel in an upright position and the panel can then be pivoted to dispose the patient in a generally prone orientation for imaging.

23 Claims, 14 Drawing Sheets

(56) References Cited

U.S. PATENT DOCUMENTS

| | | |
|---|---|---|
| 6,987,831 B2 | 1/2006 | Ning |
| 8,479,329 B2 | 7/2013 | DeBraal et al. |
| 2012/0029338 A1* | 2/2012 | Kuo .................... A61B 6/0435 600/407 |
| 2012/0069959 A1* | 3/2012 | Hoernig ............... A61B 6/0435 378/37 |
| 2018/0317867 A1 | 11/2018 | Boone |
| 2020/0170603 A1 | 6/2020 | Bailey et al. |

* cited by examiner

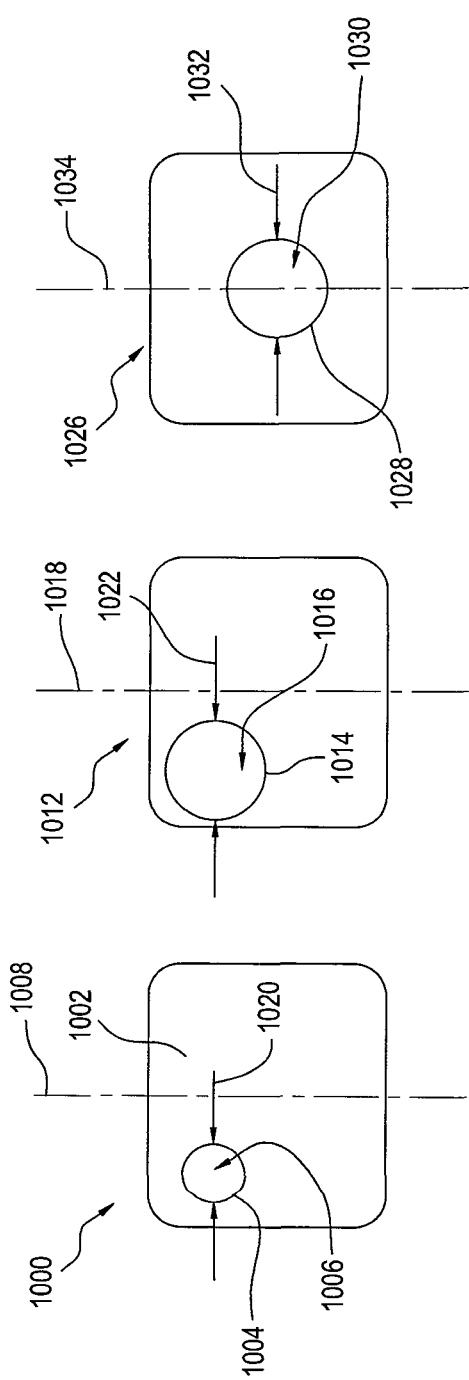
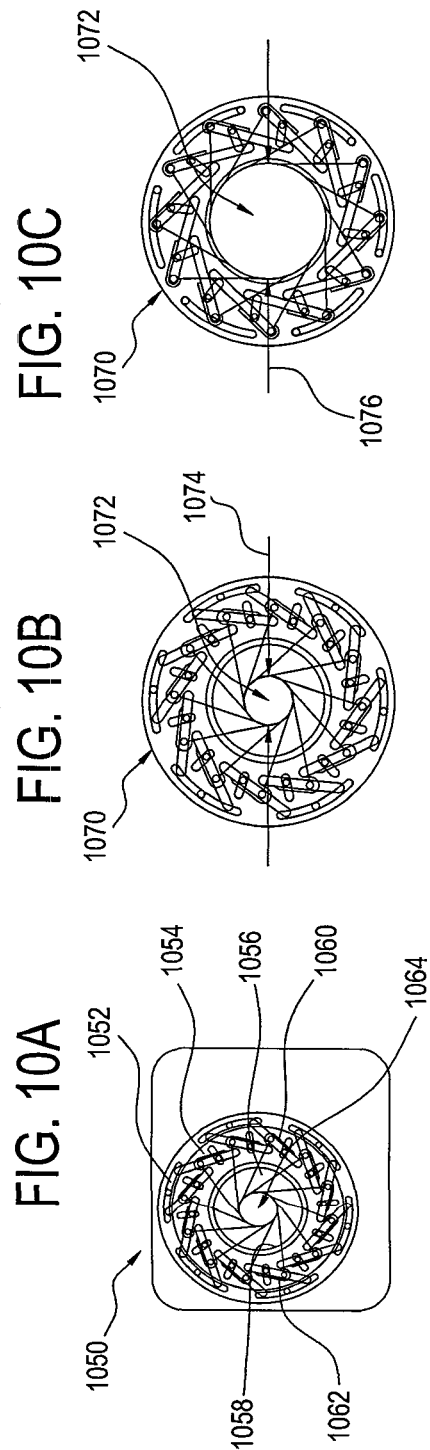

ERGONOMIC IMPROVEMENTS IN CONE BEAM BREAST COMPUTED TOMOGRAPHY

CROSS-REFERENCE TO RELATED APPLICATIONS

The present application is a continuation of PCT patent application PCT/US2023/018359 filed on Apr. 12, 2023, which claims the benefit of provisional patent applications OMNIBUS DISCLOSURE, set forth in an application for Letters Patent of the United States already filed on Apr. 14, 2022 as U.S. Provisional Application No. 63/331,153, and FIXTURING AND SUPPORT FOR MEDICAL IMAGING, set forth in an application for Letters Patent of the United States already filed on Aug. 26, 2022 as U.S. Provisional Application No. 63/401,475, and ERGONOMIC IMPROVEMENTS IN CONE BEAM BREAST COMPUTED TOMOGRAPHY, set forth in an application for Letters Patent of the United States already filed on Aug. 26, 2022 as U.S. Provisional Application No. 63/401,493, and STATIONARY DETAIL IMAGING IN CONE BEAM BREAST COMPUTED TOMOGRAPHY, set forth in an application for Letters Patent of the United States already filed on Aug. 26, 2022 as U.S. Provisional Application No. 63/401,513, and CONE BEAM BREAST COMPUTED TOMOGRAPHY WITH PATIENT SUPPORT SUBSYSTEM, set forth in an application for Letters Patent of the United States already filed on Aug. 26, 2022 as U.S. Provisional Application No. 63/401,546, and, CONE BEAM BREAST COMPUTED TOMOGRAPHY WITH PIVOTAL GANTRY SUBSYSTEM, set forth in an application for Letters Patent of the United States already filed on Aug. 26, 2022 as U.S. Provisional Application No. 63/401,548, and ULTRASONIC HYBRID IMAGING IN CONE BEAM BREAST COMPUTED TOMOGRAPHY, set forth in an application for Letters Patent of the United States already filed on Dec. 6, 2022 as U.S. Provisional Application No. 63/430,571, the disclosures of all of which are herewith incorporated by reference in their entireties.

FIELD OF THE INVENTION

The present invention relates to the field of cone beam tomographic imaging, and in particular to the field of patient ergonomics in cone beam breast tomographic imaging.

SUMMARY

According to the National Cancer Institute, one out of eight women will be diagnosed with breast cancer in her lifetime. And while a reduction in mortality from breast cancer is evident in published reports, each year 40,000 women will die of the disease.

The optimal breast imaging technique detects tumor masses when they are small, preferably less than 10 mm in diameter. It is reported that 93% of women with mammographically detected invasive breast carcinoma 1-10 mm have a 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Although mammography, which on average can detect cancers about 12 mm in size, was the most effective tool for the early detection of breast cancer previously available, mammography has relatively low sensitivity to small breast cancers (under several millimeters). Specificity and the positive predictive value of mammography remain limited owing to structure and tissue overlap.

The limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers.

The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large-scale clinical trial, the Digital Mammographic Imaging Screening Trial (DMIST), showed that the rates of false positives for DM and SFM were the same.

The relatively low specificity of mammography leads to biopsy for indeterminate cases, despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

To address the mammography limitations indicated above, one of the inventors has previously developed a cone beam breast computed tomography (CBBCT) system. Briefly, the major features of existing CBBCT include a horizontal, ergonomically designed patient table with a modular insert to optimize coverage of the uncompressed breast, including the chest wall; wide openings (1 m) on each side of the patient table for easy access to the breast for positioning and potentially good access for imaging-guided biopsy and other procedures without significantly changing the basic platform; and slip-ring technology that facilitates efficient dynamic contrast imaging studies and angiogenesis imaging in the future.

The results of phantom studies indicate that CBBCT can achieve a spatial resolution up to about 2.8 lp/mm, allowing detection of a 2 mm carcinoma and microcalcifications about 0.2 mm in size for an average size breast (about 13 cm in diameter at the chest wall) with a total dose of about 5 mGy. This dose is less than that of a single mammography exam, assuming two views are required for each breast.

The image quality of CBBCT for visualizing breast tissues, breast tumors and calcifications is excellent, and coverage of the breast, including the chest wall region, is at least equivalent to mammography. Visualization of major blood vessels is very good without using a contrast agent. Accordingly, CBBCT offers significant improvement in detecting and biopsying suspected lesions in a patient.

While the imaging benefits of CBBCT are remarkable, in many ways, the ergonomic advantages of the technology are just as important. For example, in many CBBCT procedures, an image can be acquired without requiring the heavy compression of the breast tissue generally associated with mammography.

It is characteristic of mammography, for example, that breast imaging is preceded by insertion of a patient's breast into a fixturing apparatus that significantly compresses breast tissue in a direction transverse to a breast longitudinal axis. Patients widely report physical and psychological discomfort related to the degree of compression required for conventional mammography, and studies have shown that this discomfort is a contributing factor to low rates of screening and diagnostic mammography among patients generally and, in particular, among some ethnic and cultural populations.

Moreover, the breast compression associated with mammography can result in a displacement of breast tissue that makes the later localization of features such as lesions and calcifications, for purposes of biopsy and lumpectomy procedures, more difficult.

Additional improvements in CBBCT imaging presented herewith offer the potential to expand on its imaging benefits and offer ergonomic improvements that are likewise highly beneficial. Among these improvements are technical improvements, and methods and apparatus that facilitate presentation of the patient to the CBBCT system. These include loading apparatus, patient seating facilities, and equipment arrangements and configurations that improve comfort and ease of presentation of the patient to the machine for both the patient, and for technical and medical personnel.

In current practice, a patient undergoing CBBCT lies prone on a table. A subject breast is disposed downward through an aperture in an upper surface of the table, depending from the chest wall into an imaging chamber disposed under the table. The position of the breast within the imaging chamber is maintained by the patient remaining stationary as the patient lies on the surface of the table.

An imaging apparatus is coupled to a mobile gantry which is supported on a bearing device for rotation about an axis of rotation. The axis of rotation is disposed in a generally vertical orientation and passes through the aperture of the table. Preferably, an approximate centroid of the breast to be imaged is arranged such that the axis of rotation passes through the approximate centroid.

During imaging, the mobile gantry rotates around the axis of rotation, bringing the imaging apparatus through at least a portion of a circular path. As it traverses this path, the imaging apparatus emits a series of x-ray pulses and captures corresponding image data which is processed to prepare a tomographic model of the breast.

Notwithstanding the many benefits and advantages of CBBCT, there are some patients who find it difficult or impossible to assume a prone position on a patient table. Such patients may be unable to locate themselves properly on the table, or to dispose the breast to be imaged through the aperture as necessary. Patients who are elderly, obese, pregnant, or disabled, as well as those suffering from paralysis or amputation, among other ailments, are among the many for whom the act of climbing onto a table and lying down in a specific prone position is prohibitively difficult.

The inventors of the present invention, having given long and careful consideration to the problems associated with breast imaging, with CBBCT imaging and, in particular, to questions of CBBCT ergonomics, have developed new and useful systems, apparatus and methods that represent a substantial improvement over previously known approaches. The present invention includes apparatus, and corresponding systems and methods, for the entry of the patient into the CBBCT system, and for support of the patient during the tomographic imaging process.

Accordingly, in certain embodiments of the present invention, a CBBCT system is provided that is arranged for upright patient entry and subsequent automatic repositioning of the patient into a scanning orientation. In certain embodiments of the invention, a patient is provided with a saddle for support during upright entry and prior to patient reorientation. In certain embodiments of the invention, a patient interface panel is arranged to pivot between a vertical orientation and a horizontal orientation so as to facilitate patient entry. In certain embodiments of the invention, the patient interface panel is adapted to move pivotally away from a vertical orientation into a horizontal orientation, where it serves as a patient table once a patient is positioned for scanning. In certain embodiments of the invention, the patient stands on a patient step supported by the patient interface panel.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent to one skilled in the art, however, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art will appreciate that the figures taken together reflect various aspects and embodiments exemplifying the invention.

Correspondingly, references throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" at various places throughout the specification are not necessarily all referring to the same embodiment. Furthermore, the particular features, structures, or characteristics will be combined in any suitable manner in one or more embodiments.

BRIEF DESCRIPTION OF THE DRAWINGS

FIG. 10A shows, in schematic proximal elevation, certain features of a CBBCT imaging system prepared according to principles of the invention, including exemplary subpanel elements;

FIG. 10B shows, in schematic proximal elevation, additional aspects of a CBBCT imaging system prepared according to principles of the invention, including exemplary subpanel elements;

FIG. 10C shows, in schematic proximal elevation, further exemplary aspects of a CBBCT imaging system prepared according to principles of the invention, including exemplary subpanel elements;

FIG. 10D shows, in schematic proximal elevation, certain features of a CBBCT imaging system prepared according to principles of the invention, including exemplary adjustable subpanel elements;

FIG. 10E shows, in schematic proximal elevation, further details and configurations of a CBBCT imaging system prepared according to principles of the invention, including exemplary adjustable subpanel elements;

FIG. 10F shows, in schematic proximal elevation, additional configurations of a CBBCT imaging system prepared according to principles of the invention, including exemplary adjustable subpanel elements;

DETAILED DESCRIPTION

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the substance disclosed.

It should be noted that while any of the embodiments described for exemplary purposes below will identify specific elements and combinations of elements, these examples are not intended to be determinative. Rather, discrete elements will, in appropriate circumstances, be combined into integral elements and/or assemblies. Further, the present disclosure of aspects and features of particular elements described herewith as integral, should be understood to convey also the disclosure of individual elements and assemblies providing the same characteristics and/or functionality.

Figure 1:
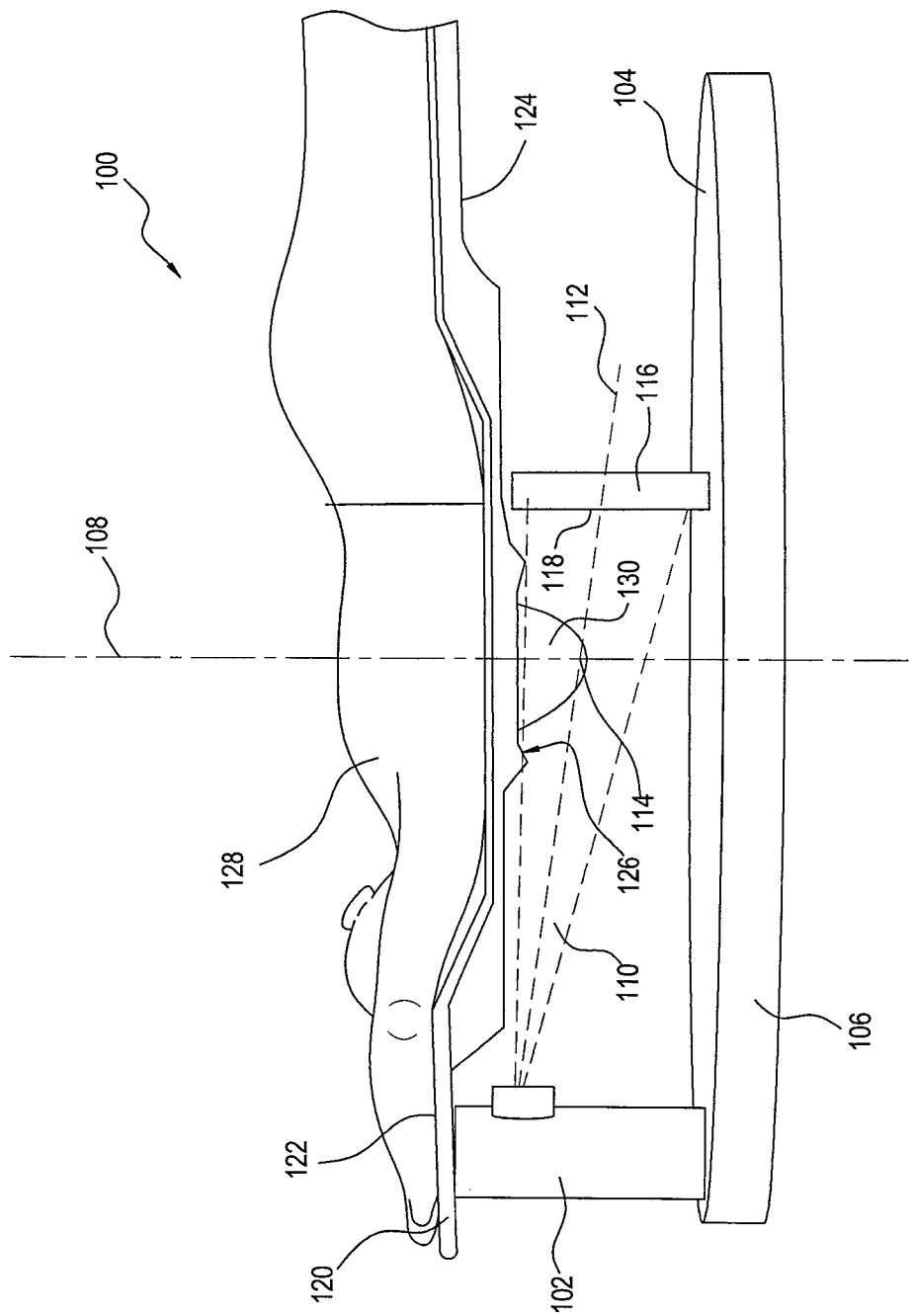
FIG. 1 shows, in cutaway perspective view, a portion of an exemplary CBBCT imaging system.

FIG. 1 shows, in cutaway perspective view, a portion of an exemplary CBBCT imaging system 100, prepared according to principles of the invention. The system 100 includes an x-ray source 102. The x-ray source 102 is mounted on an upper surface 104 of a rotating gantry 106. The rotating gantry 106 is supported by a bearing, and arranged for rotation about an axis of rotation 108.

The x-ray source 102 is configured to emit a beam of x-rays 110. The beam of x-rays 110 defines a beam longitudinal axis 112 that, in the illustrated embodiment, intersects (at 114) the axis of rotation 108.

In certain embodiments of the invention, beam 110 is configured as a cone beam. In certain configurations, a cross-section of the beam 110 taken transverse to the longitudinal axis 112 defines a disk of substantially uniform x-ray intensity with a substantially circular perimeter.

In other configurations within the scope of the invention, a cross-section of the beam 104 taken transverse to the longitudinal axis 112 defines a region of substantially uniform x-ray intensity with a substantially circular perimeter save for a portion of the disc outwardly of a chord of said circular perimeter. As will be appreciated on consideration of the further disclosure below, in certain embodiments, the chord will be disposed in generally parallel spaced relation to a lower surface of a patient table.

Accordingly, in certain configurations, a cross-section of the beam 110 taken transverse to the longitudinal axis 112 defines a truncated disk of substantially uniform x-ray intensity with a substantially truncated circular perimeter (i.e., a perimeter that is circular except for a horizontal chord of the circle at its upper periphery). This configuration optimizes imaging of the breast while minimizing irradiation of chest wall tissue above the breast. It is implemented, in certain embodiments, by the placement of an x-ray-opaque collimating plate across a portion of an otherwise circular-cross-section beam generated by the x-ray source.

In still further configurations within the scope of the invention, a cross-section of the beam 110 taken transverse to the longitudinal axis 112 defines a region of substantially uniform x-ray intensity with a polygonal perimeter, where the polygonal perimeter will, in respective embodiments and configurations, include any of a triangular perimeter, a rectangular perimeter (including, without limitation, a square perimeter), a pentagonal perimeter, a hexagonal perimeter, a perimeter of any higher order geometric shape, or a perimeter having any arbitrary curve or combination of line segments and curves according to the demands of a particular application. Moreover, it will be appreciated that any of the cross-sectional configurations described above may define a beam having a nonuniform intensity including, without limitation an intensity that falls to zero in a region, or certain regions, of the cross-section.

An x-ray detector 116 is also mounted on the upper surface 104 of the rotating gantry 106. In one exemplary embodiment, the x-ray detector 116 includes a flat panel detector having a generally planar receiving surface 118. Receiving surface 118 is disposed generally transverse to longitudinal axis 112 and on the opposite side of axis of rotation 108 from the x-ray source 102. It will be appreciated by one of skill in the art that the configuration described is merely exemplary of many possible arrangements in which the x-ray source, the x-ray detector, and any other component of the system, maybe supported from above, from a side, or in any other way appropriate to achieving the desired function, and that the shape and configuration of the gantry, and of the x-ray detector, will likewise assume any form in respective embodiments of the invention.

Rotation of the gantry 106 about axis of rotation 108 during operation of the imaging system 100 will result in the receiving surface 118 following a transit path about axis of rotation 108. In a typical configuration, the transit path will include at least a portion of a circle disposed transverse to, and centered at, axis of rotation 108. It should be noted, however, that other transit paths are considered to be within the scope of the invention, and to be disclosed herewith.

In certain embodiments of the invention, one or both of the x-ray source 102 and the x-ray detector 116 are arranged so that their respective positions on the upper surface 104 of gantry 106 is adjustable. For example, the x-ray source 102 and the x-ray detector 116 may be adjustable together or independently in a radial direction with respect to axis of rotation 108, in a circumferential direction with respect to axis of rotation 108, in a direction towards or away from gantry surface 104, or in any other manner deemed beneficial by the designer or user of a particular apparatus embodying the invention.

A patient table (or patient interface panel) 120 includes an upper surface 122 and a lower surface 124. An aperture 126 communicates between the upper surface 122 and lower surface 124 of the table. The upper surface 122 is arranged to support a patient 128, typically with the patient lying prone on the surface 122, as illustrated. In this arrangement, a breast 130 of the patient is disposed pendant from the patient's chest wall downwardly through aperture 126.

In operation, the gantry rotates about axis of rotation 108, carrying x-ray source 102 and x-ray detector 116 in transit in a path around the patient's breast. During this transit, x-ray image data is captured by operation of the x-ray detector 116 in conjunction with corresponding interface electronics and computer systems. The x-ray image data corresponds to a plurality of x-ray images taken at respective angular locations about axis of rotation 108. Taken together, the x-ray image data, or a subset of the same, is processed to provide information about the internal state and condition of the breast.

Figure 2:
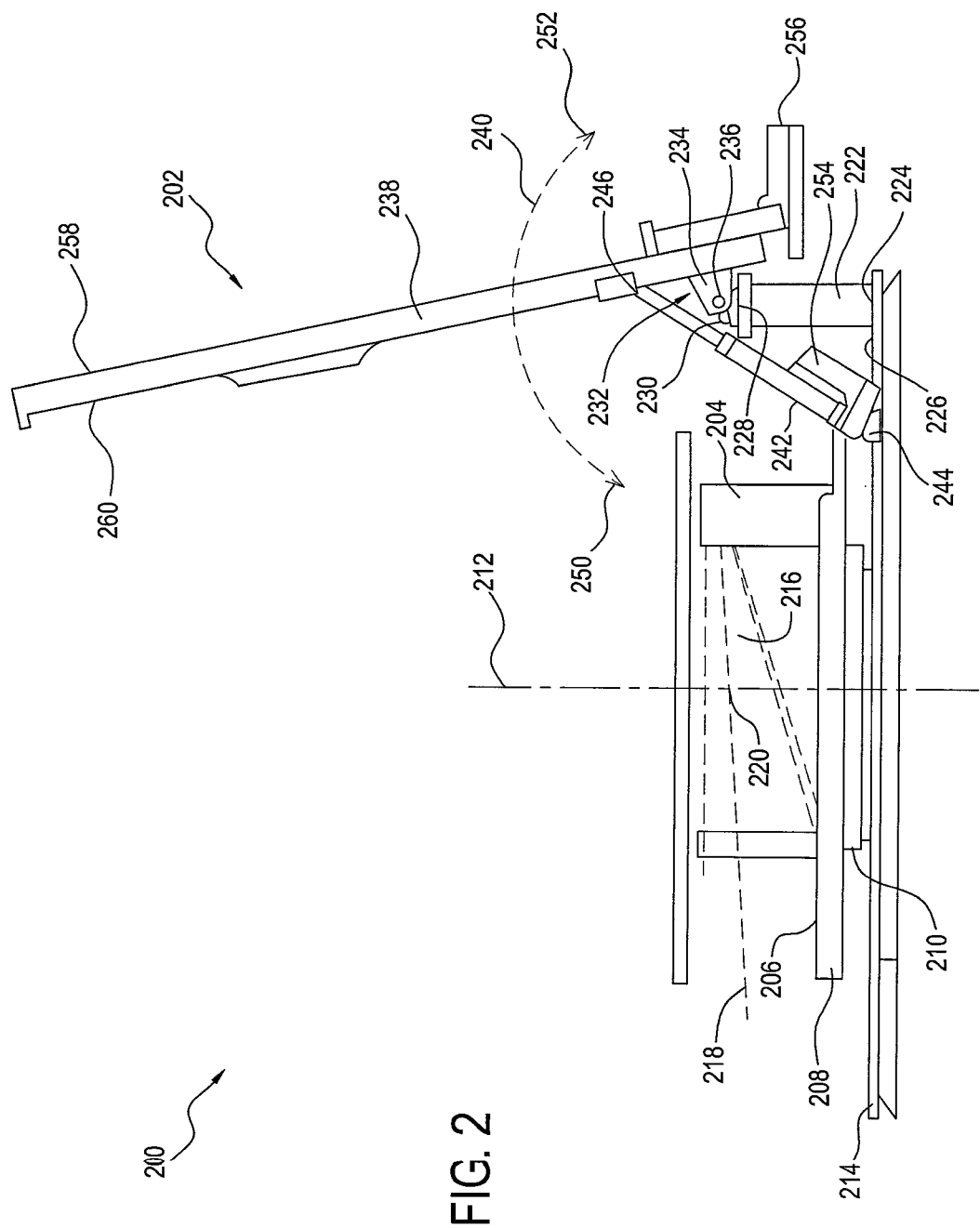
FIG. 2 shows, in schematic side elevation, certain aspects of an exemplary CBBCT imaging system, including a pivotable patient interface panel prepared according to principles of the invention.

FIG. 2 shows, in schematic side elevation, a portion of an exemplary CBBCT imaging system 200, including an ergonomic assist subsystem 202. Like system 100 described above, system 200 includes an x-ray source 204. The x-ray source 204 is mounted on an upper surface 206 of a rotating gantry 208. The rotating gantry 208 is supported by a bearing 210, and arranged for rotation about an axis of rotation 212. The bearing 210 is, in turn, supported on a base member 214 of the imaging system 200.

The x-ray source 204 is configured to emit a beam of x-rays 216. The beam of x-rays 216 defines a beam longitudinal axis 218 that, in the illustrated embodiment, intersects (at 220) the axis of rotation 212.

In the exemplary embodiment presented here, the ergonomic assist subsystem 202 includes a structural column 222 coupled at a lower end 224 thereof to an upper surface region 226 of the base member 214. An upper end 228 of the structural column 222 includes a first hinge flange 230 of a hinge feature 232. A second hinge flange 234 of the hinge feature 232 is pivotally coupled to the first hinge flange 230 by a hinge pin 236.

The ergonomic assist subsystem 202 includes a patient table (or patient interface panel) 238. Patient table 238 is coupled to and supported by hinge flange 234 for pivotal motion 240 about a longitudinal axis of hinge pin 236. A linear actuator 242 is coupled at a lower end 244 to base member 214, and at an upper end 246 thereof to the patient table 238. In operation, a length of the linear actuator 242 between the lower end 244 and the upper end 246 is controllable, such that shortening the linear actuator 242 tends to pivot the table 238 downward 250 whereas lengthening the linear actuator 242 tends to pivot the table 238 upward 252.

In the illustrated embodiment, the linear actuator includes an electric motor 254 that, by its operation, tends to effect the above-described shortening and lengthening of the linear actuator 242. One of skill in the art will appreciate, however, that any number of linear actuators, rotary actuators, or other operative mechanisms and arrangements will be employed in corresponding embodiments of the invention.

Thus, for example, in certain embodiments of the invention, the linear actuator will include one or more of an electrical solenoid, a pneumatic cylinder, a hydraulic cylinder, a pneumatic bladder, a hydraulic bladder, a linear electric motor, a rotary electric motor, an Acme screw and nut, a lead screw, a ballscrew, a cable, a pulley, a timing belt, a timing pulley, an appropriately sized worm gear reducer, a rack and pinion assembly, a rack and worm gear assembly, and any other appropriately functioning actuator component that is known or becomes known in the art.

The ergonomic assist subsystem 202 also includes a patient step assembly 256. In the illustrated embodiment, patient step assembly 256 is coupled to, and supported by, patient table 238. The patient table 238 includes an upper surface region 258. A lower surface region 260 of the patient table 238 is disposed in substantially parallel spaced relation to upper surface region 258. As will be further discussed below, in the operation of the ergonomic assist subsystem 202, the patient table 238 and patient step assembly 256 cooperate to support a patient, and position the patient, for CBBCT imaging.

Figure 3:
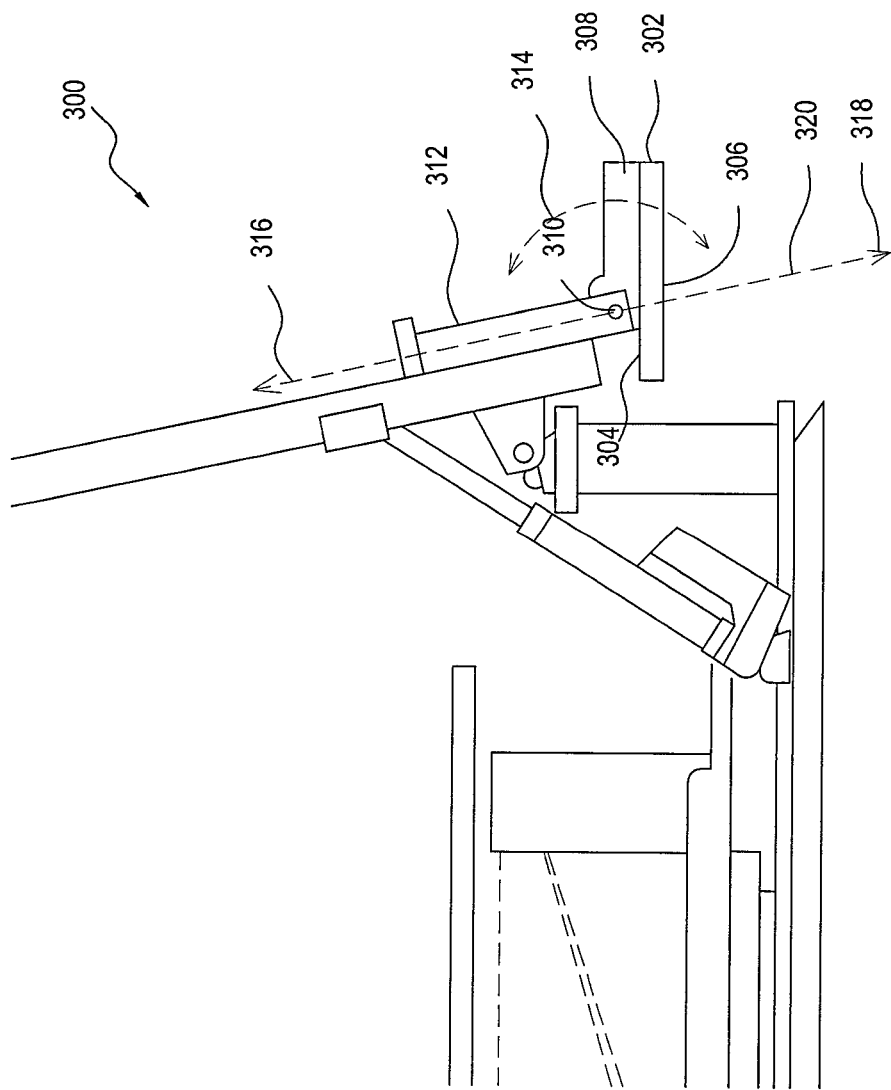
FIG. 3 shows, in schematic side elevation, additional aspects and features of an exemplary CBBCT imaging system, including a patient step for a pivotable patient interface panel prepared according to principles of the invention.

FIG. 3 shows, in schematic side elevation, additional detail of an exemplary patient step assembly 300 like that shown 256 in relation to the ergonomic assist subsystem 202 of FIG. 2. The patient step assembly 300 includes a step member 302 with an upper surface region 304 and a lower surface region 306. In the illustrated embodiment, the upper 304 and lower 306 surface regions are disposed in generally parallel spaced relation to one another. The reader will understand, however, that other configurations are possible and intended to be taught by the present disclosure.

In one configuration, as illustrated, upper surface 304 is disposed in a generally horizontal orientation. As will be further discussed below, however, this orientation is adapted to be modified during operation of the CBBCT system and, in particular, during operation of the ergonomic assist subsystem.

In the exemplary embodiment illustrated, the patient step assembly 300 includes a flange portion 308. The flange portion 308 is pivotally coupled through a bearing member 310 to a linear bearing assembly 312. The flange portion 308 is also substantially fixedly coupled to the step member 302 so that the step member 302 is supported by the linear bearing assembly 312.

Depending on the needs of a particular application or embodiment of the invention, the bearing member 310 may be a hinge pin, a shaft, a rotary bearing assembly, a flexible living hinge, or any other device known in the art, or yet to be discovered, that serves to permit an adjustable pivotal motion 314 of the flange portion 308. Consequently, the combination of the pivotal coupling of the flange portion 308 through the bearing member 310 to the linear bearing assembly 312 permits the upper surface 304 of the step member 302 to be adjustably positioned by motion 314 in a manner that will be further described below.

The linear bearing assembly 312 is also adjustable upwardly 316 and downwardly 318 along a longitudinal axis 320 thereof to provide a corresponding adjustment of the flange portion 308 the step member 302 and ultimately, upper surface 304 of the step member 302. As will be seen below, this adjustability is advantageous for the operative positioning of a patient with respect to the CBBCT system.

It will be appreciated that the linear bearing assembly 312 will, in certain embodiments include any of a wide variety of actuators and actuator mechanisms such as, for example, an electrically, mechanically, pneumatically or hydraulically operated linear actuator in the nature of any of those described above, as well as any of a wide variety of manual actuators such as, for example, a handcrank and/or a ratchet lever. Likewise, the bearing member 310 will also be, in exemplary embodiments, be operated by any of a wide variety of actuators and actuator mechanisms such as, for example, an electrically, mechanically, pneumatically or hydraulically operated linear actuator in the nature of any of those described above, as well as any of a wide variety of manual actuators such as, for example, a handcrank and/or a ratchet lever.

Figure 4:
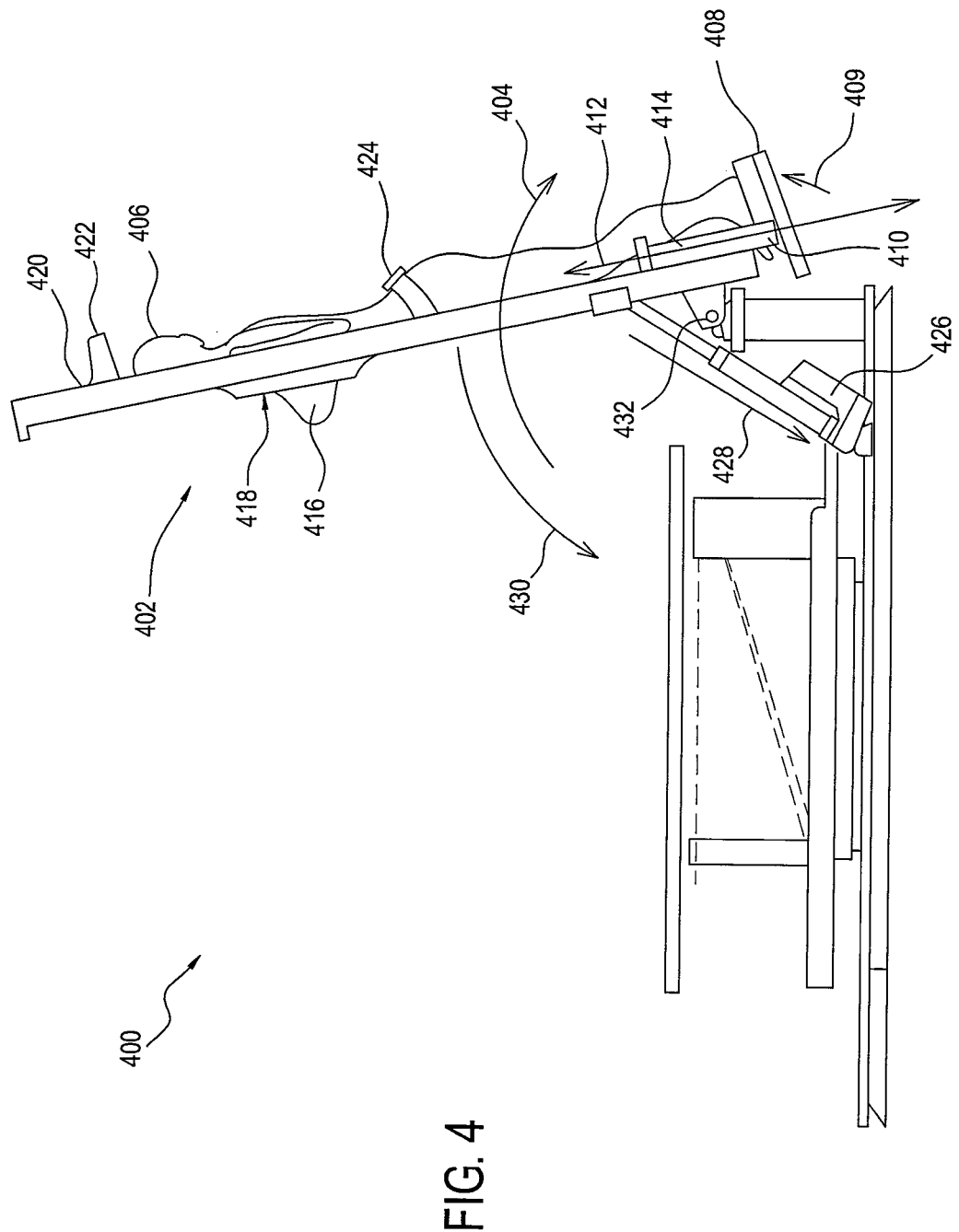
FIG. 4 shows, in schematic side elevation, additional aspects and configurations of an exemplary CBBCT imaging system, prepared according to principles of the invention.

FIG. 4 shows, in schematic side elevation, a portion of an exemplary CBBCT imaging system 400, including an ergonomic assist subsystem 402 similar to the subsystem 202 of FIG. 2. In the illustration, the ergonomic assist subsystem 402 is shown in a fully elevated state, i.e., at an extreme position in direction 404.

A patient 406 is shown disposed on the ergonomic assist subsystem 402. The ergonomic assist subsystem 402 has been adjusted to achieve the comfort and correct positioning of the patient 406. Accordingly, step member 408 has been pivoted upwardly 409 (or downwardly) about a bearing member 410.

In addition, the step member 408 has been raised or lowered 412 by operation of a linear bearing assembly 414 so as to adjust a position of the patient 406 such that a breast 416 of the patient is properly positioned for imaging within an aperture 418 of a patient table (or patient interface panel) 420.

It will be appreciated by one of skill in the art that, in various aspects and modes of operation of the invention as exemplified in the system 400, adjustment of the various controllable degrees of freedom of the system can be made before or after or both before and after the patient 406 has stepped onto the step member 408, and thus mounted the ergonomic assist subsystem 402.

In certain embodiments of the invention, various apparatus will be provided for the safety and convenience of the patient including, for example, grip handles, e.g. 422, safety straps, e.g., 424, a safety bar (not shown) with or without positive adjustment features (not shown) that serve to ensure that the patient, once mounted on the ergonomic assist subsystem 402 will not inadvertently fall from the system.

Having disposed the patient 406 on the ergonomic assist subsystem 402, the linear actuator 426 is operated so as to shorten 428 the operative length of the linear actuator, and cause the patient table 420 to pivot 430 about hinge or bearing 432.

Figure 5:
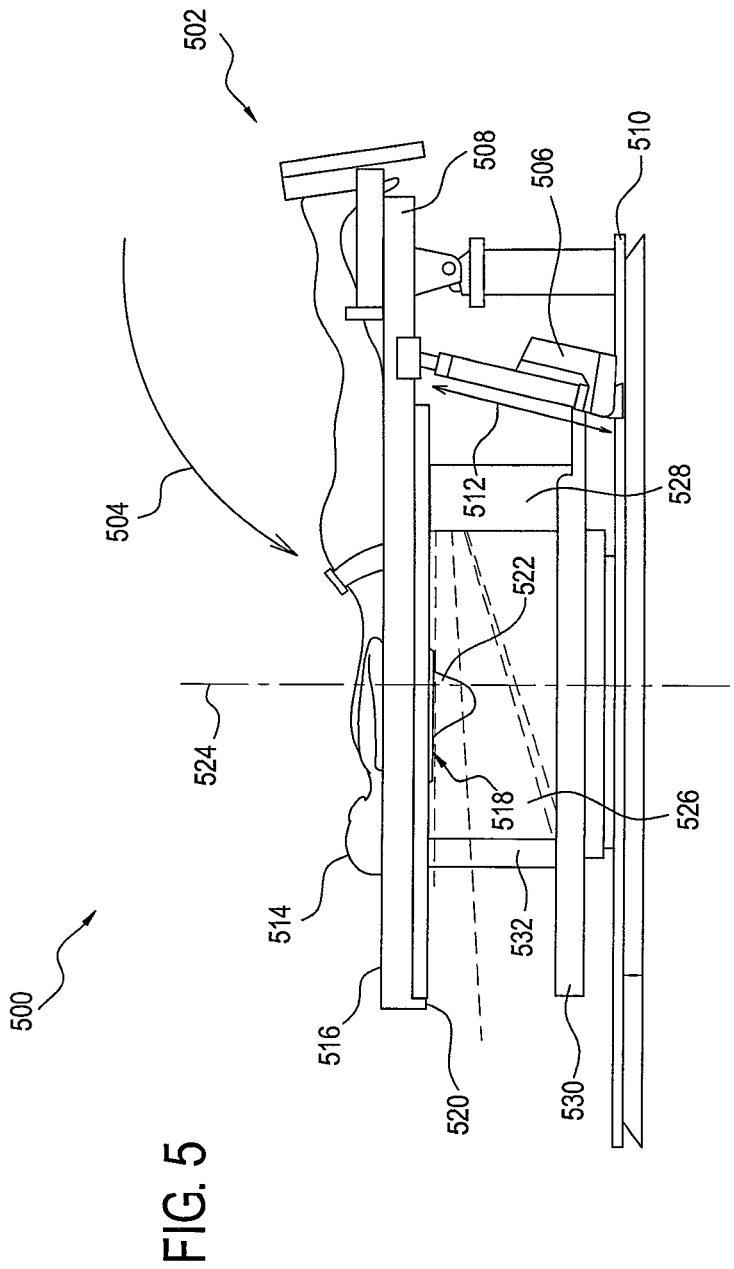
FIG. 5 shows, in schematic side elevation, additional aspects and configurations of an exemplary CBBCT imaging system, prepared according to principles of the invention.

In a typical operation of the ergonomic assist subsystem 402, operation of the linear actuator 426 continues, and the patient table 420 proceeds to pivot 430, until the patient is disposed in a generally horizontal orientation, as shown in FIG. 5.

Accordingly, FIG. 5 shows, in schematic side elevation, a portion of an exemplary CBBCT imaging system 500, including an ergonomic assist subsystem 502 similar to the subsystem 402 of FIG. 4. In the illustration, the ergonomic assist subsystem 502 is shown in a fully descended state, i.e., at an extreme position in direction 504. Consistent with this state, a linear actuator assembly 506 (coupled between a patient table (or patient interface panel) 508 and a base member 510 of the imaging system 500) is disposed in a state of minimum length 512.

A patient 514 is disposed lying in a prone position on (what is, in the illustrated descended state) an upper surface 516 of patient table 508. The patient table 508 includes an aperture 518 between upper surface 516 and a lower surface 520 of the patient table 508.

A breast 522 of patient 514 is disposed pendant from a chest wall of the patient through aperture 518, and is thus positioned for imaging. Accordingly, an approximate centroid of the breast 522 is disposed coincident with an axis of rotation 524 of a rotating gantry 530 of the CBBCT imaging system 500.

The reader will appreciate that the details of the CBBCT system 500 will vary according to the configuration and requirements of a particular embodiment of the invention, in the exemplary system 500 provided here, the illustrated positioning of the breast places it advantageously in an operative location within an x-ray beam 526 produced by an x-ray source 528. The x-ray source 528 is coupled to, and supported by, rotating gantry 530 for controlled rotation about the axis of rotation 524.

Similarly, an x-ray imager 532 is coupled to and supported by rotating gantry 530 in a location effective to capture an image of the breast 522. One of skill in the art will readily understand that the particular arrangement of the imaging components will vary from embodiment to embodiment, and that aspects of any of systems 100-400 described are intended to be incorporated in the present disclosure where appropriate.

After imaging of the breast 522 is completed, and responsive to an input from a technician, further operation of the linear actuator assembly 506 will cause the linear actuator to resume its extended length such that the patient table 508 resumes its fully elevated state, as exemplified in FIG. 4.

Figure 6A:
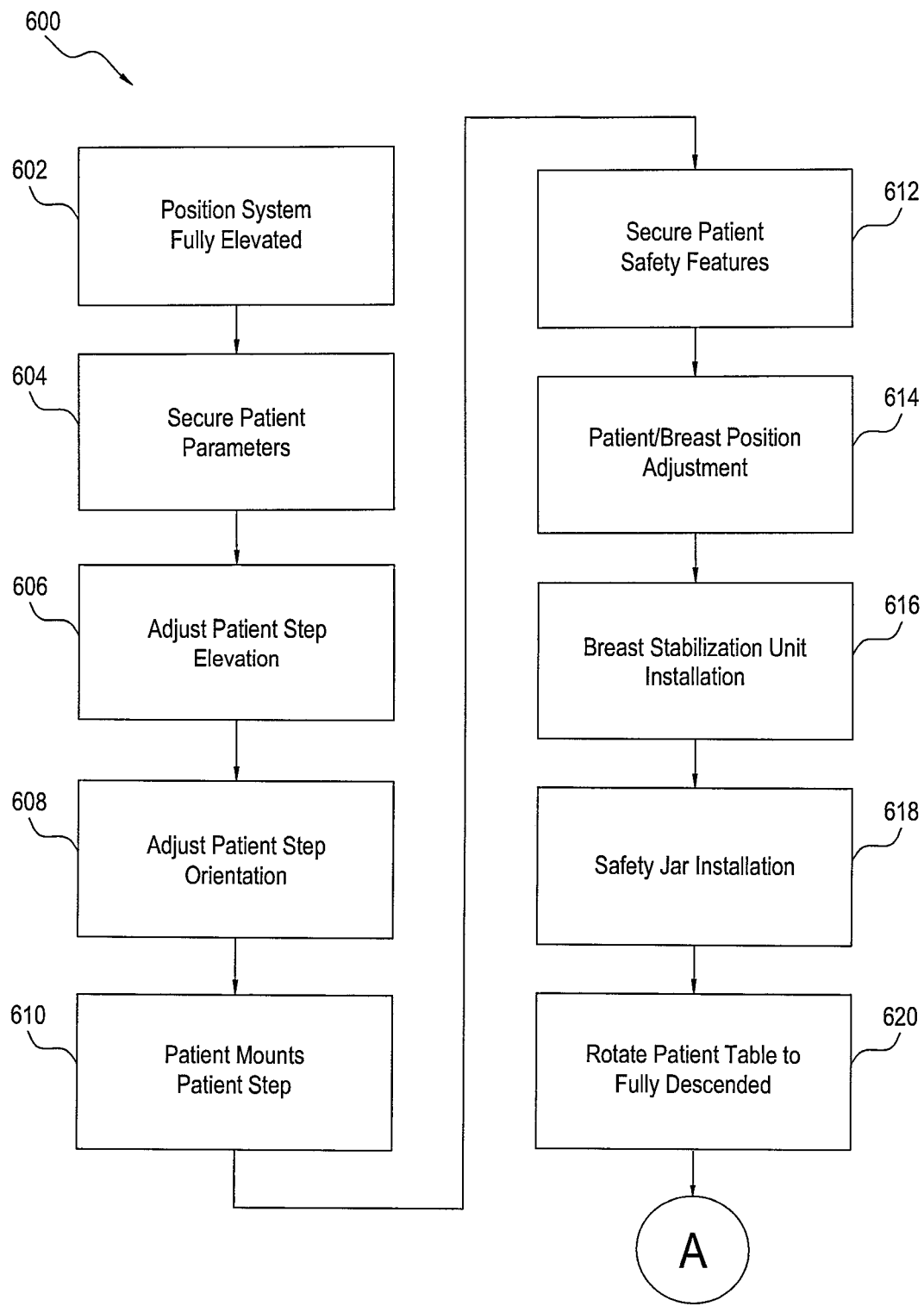
FIG. 6A shows, in functional block diagram form, certain aspects of processes and methods for using a CBBCT imaging system prepared according to principles of the invention.
Figure 6B:
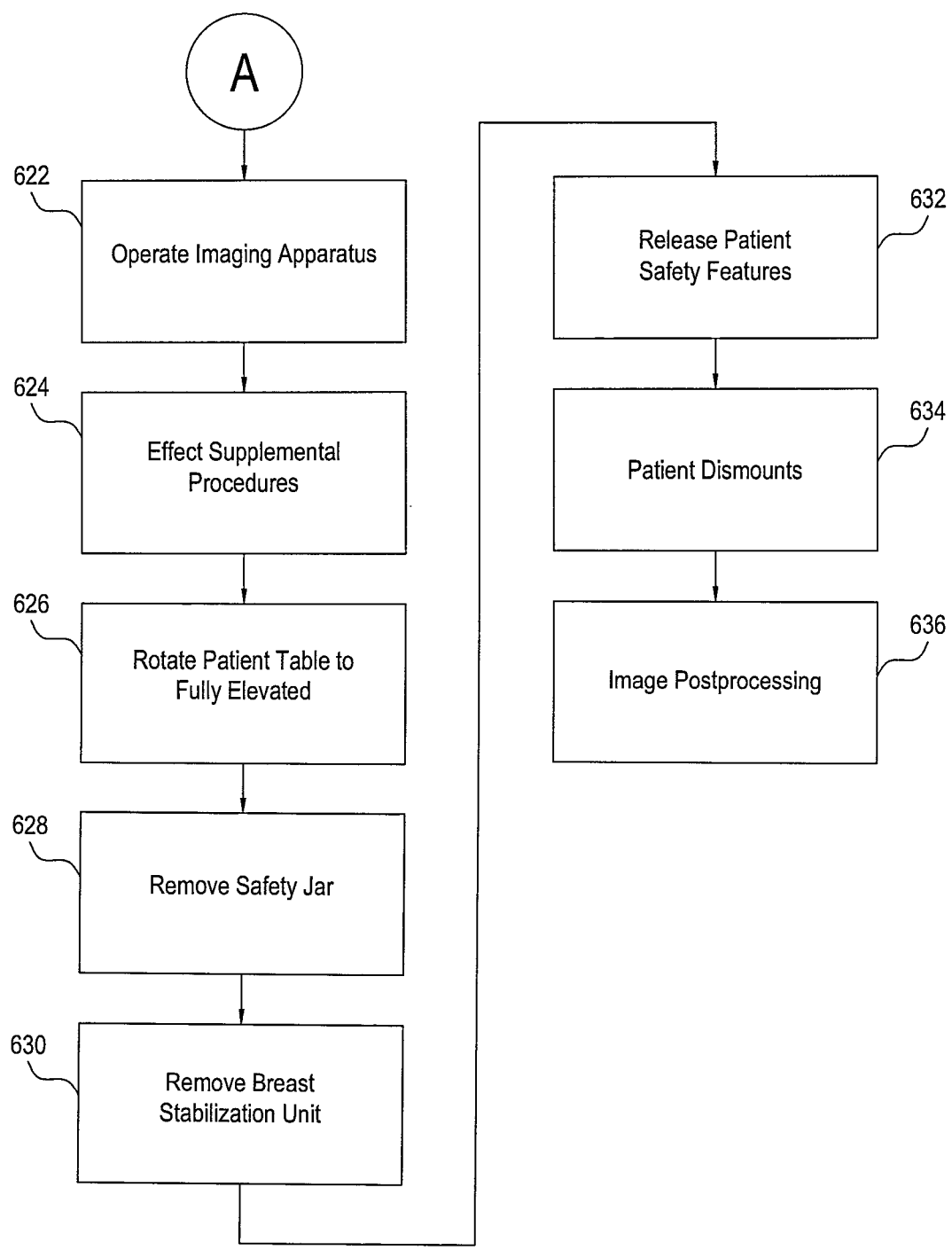
FIG. 6B shows, in functional block diagram form, additional aspects of processes and methods for using a CBBCT imaging system prepared according to principles of the invention.

FIGS. 6A and 6B are herewith considered concurrently and show, in functional block diagram form, a method 600 of operating a CBBCT imaging system including an ergonomic assist subsystem, as illustrated, for example, in FIGS. 2-5. Accordingly, prior to operation of the ergonomic assist subsystem, the subsystem is configured in its fully elevated state 602.

Patient parameters (such as e.g., breast height with respect to patient feet) are secured 604, either by manual measurement of the patient, by extraction from patient medical records, or by automatic measurement. The parameter values, once secured, are optionally used to set the position of the patient step, adjusting its elevation 606 and its orientation 608 (one or both or neither), as discussed above. The patient then mounts the step 610 and leans into the patient-facing surface of the patient table.

Alternately, in certain embodiments of the invention, the patient steps onto the patient step. Thereafter, the height and orientation of the patient step are adjusted with the patient disposed in situ, and the necessary positioning (i.e., patient parameters) are ascertained from manual observation or automatic sensing of the patient body with respect to the system. In other words, the patient step is adjusted until the patient breast is properly situated within the table aperture.

Before or after adjustment, the patient is optionally secured to the table 612 employing one or more safety features. Safety features include, for example, a strap or belt, a locking bar disposed behind the patient's back, a hook and loop (e.g., Velcro™) interface between the table and one or more straps or garments donned by the patient in advance and including corresponding hook and loop elements. It will be appreciated by one of skill in the art that, in certain embodiments one or more safety features are engaged as soon as the patient steps onto the step. In other embodiments, a safety feature will be engaged after positioning of the patient is complete.

Where advantageous, the position and orientation of the patient breast to be image is then adjusted 614 for optimum imaging. In certain embodiments of the invention, a breast stabilization unit is applied to the breast 616 to support and stabilize the breast during imaging.

Where advantageous, a safety jar is installed 618 about the breast to positively separate the breast to be imaged from rotating machinery of the CBBCT imaging system.

Once the patient is positioned and preparations are complete, the patient table is rotated 620 to its fully descended state. The imaging apparatus is then operated 622 to acquire CBBCT image data.

In certain embodiments, the image data is immediately processed and used to identify characteristics of the breast including, for example, calcifications and lesions. In some circumstances these represent newly identified breast features. In other circumstances the CBBCT image data is used to precisely locate features previously discovered and, in some instances, to guide supplemental procedures 624 such as, for example aspirated needle biopsy, or other procedures.

Naturally, these procedures are optional and applied only where indicated in relation to a particular patient. It should be further noted that in some cases, in situ breast marking, or anticipatory registration marking is effected so as to allow supplemental procedures once the table has been returned to a partially or fully elevated configuration, or even after the patient has been dismounted from the system.

In other embodiments, once imaging and supplemental procedures are complete, the table is rotated to its fully elevated position 626. Thereafter, where appropriate, the safety jar is removed 628 and the breast stabilization unit is removed 630.

Patient safety features are then released 632 and the patient dismounts the system 634. Thereafter any image postprocessing and diagnostic procedures 636 may be applied to stored data.

Figure 7:
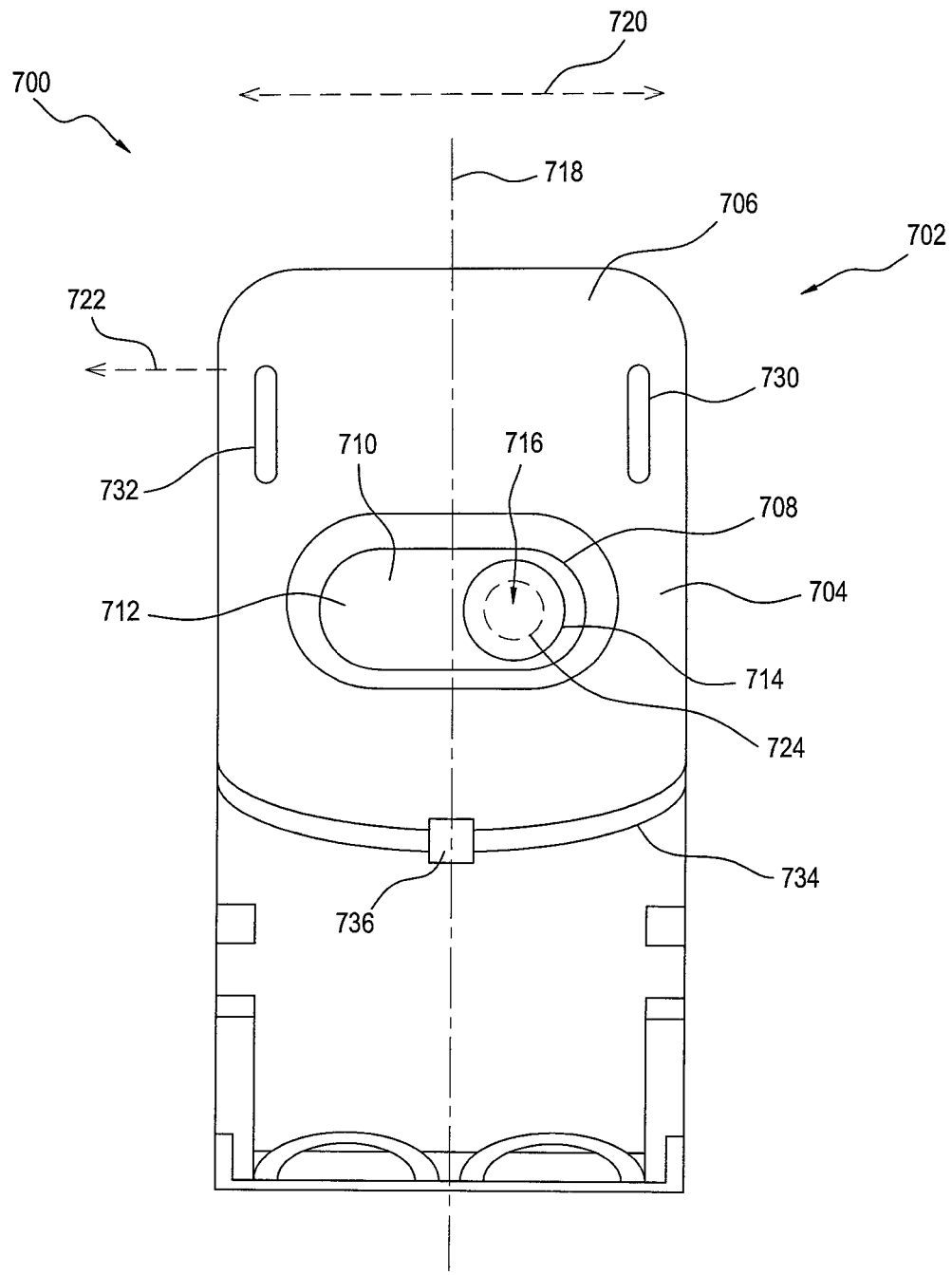
FIG. 7 shows, in schematic proximal elevation, additional aspects and configurations of an exemplary CBBCT imaging system, including a patient interface panel feature prepared according to principles of the invention.

FIG. 7 shows, in schematic proximal elevation, certain aspects of an exemplary CBBCT imaging system 700 including an ergonomic assist subsystem 702 prepared according to principles of the invention. It will be appreciated that ergonomic assist subsystem 702 is similar in its features to the systems discussed above and shows further aspects and details of the same invention. Accordingly, ergonomic assist subsystem 702 includes a patient table (or patient interface panel) 704. The patient table 704 is shown in a fully elevated position, consistent with the configuration represented in FIGS. 2 and 4 above.

The patient table 704 includes an upper surface region 706 adapted to support a patient during scanning. In various embodiments of the invention, the upper surface region 706 includes an inner circumferential edge 708 defining an aperture of the upper surface region through the patient table. In some embodiments of the invention, the aperture is adapted to receive a breast of the patient disposed therethrough. In other embodiments, including that illustrated in FIG. 7, the aperture is adapted to receive a subpanel 710 that traverses circumferential edge 708. The subpanel 710 is coupled to and/or supported by the patient table 704.

The subpanel 710 includes a subpanel surface region 712. A further inner circumferential edge 714 defines a subpanel aperture 716 through the subpanel. In the configuration illustrated, the subpanel aperture 716 is disposed to the right of a longitudinal centerline 718 of the patient table 704. Accordingly, in typical operation of the CBBCT imaging system, a right breast of the patient will be disposed through the subpanel aperture 716 during imaging.

In certain embodiments of the invention, the ergonomic assist subsystem 702 will include a lateral bearing and actuator assembly. The lateral bearing and actuator assembly is adapted to adjust a lateral position of the patient table 704. In operation, such a system will permit adjustment of the position of the table 704 in a dimension 720 transverse to the table centerline 718. This adjustment will, in advantageous applications, translate the patient's breast in a direction 722 towards a centerline of the CBBCT imaging system (i.e., towards an axis of rotation, e.g. 212 of FIG. 2 above, of a rotating gantry of the system).

One of skill in the art will appreciate that, in certain embodiments of the invention, a plurality of subpanels will be provided that include apertures of different respective dimensions. For example, a subpanel having an internal circumferential edge 724 defining an aperture with a smaller diameter (as compared with the aperture defined by inner circumferential edge 714) will be available. Accordingly, technical or medical personnel will be able to select and install a subpanel having an aperture appropriate for the size of the breast of the particular patient to be imaged.

In other embodiments of the invention, the adjustment of aperture size will be effected by operation of an adjustment mechanism such as an iris leaf diaphragm aperture mechanism. In certain embodiments the adjustment mechanism will be substantially permanently coupled to the patient table 704 of the ergonomic assist subsystem 702. In other embodiments of the invention, the adjustment mechanism will be coupled to a subpanel like subpanel 710 described above.

In certain embodiments of the invention, the aperture for receiving the breast to be imaged is disposed generally coincident with the centerline of the patient table. In such an embodiment, the patient will be positioned to align the breast to be imaged with the centerline of the table. Consequently, no additional transverse mechanism is required to align the breast with the axis of rotation of the gantry. It will be appreciated by one of skill in the art that this alignment of the breast aperture may be effected by providing the aperture directly in the patient table or, alternately, in a subpanel configured for attachment or coupling to the patient table.

Figure 8:
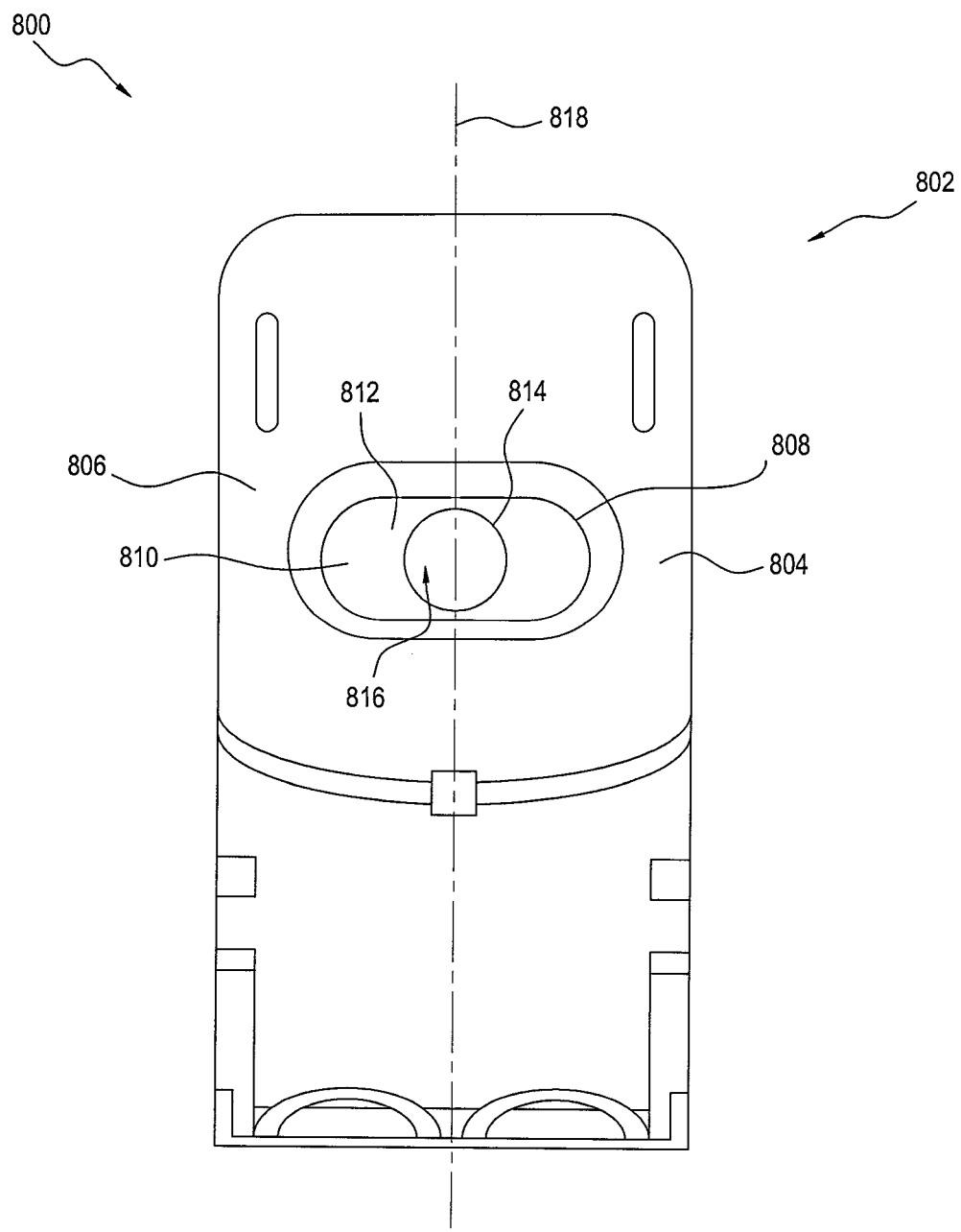
FIG. 8 shows, in schematic proximal elevation, still further aspects and configurations of an exemplary CBBCT imaging system, including a patient interface panel feature prepared according to principles of the invention.

Accordingly, FIG. 8 shows, in schematic front elevation, certain aspects of an exemplary CBBCT imaging system 800 including an ergonomic assist subsystem 802 generally similar to ergonomic assist subsystem 702 of FIG. 7. Ergonomic assist subsystem 802 includes a patient table (or patient interface panel) 804. The patient table 804 is shown in a fully elevated position, consistent with the configuration represented in FIG. 7 above.

The patient table 804 includes an upper surface region 806 adapted to support a patient during scanning. In various embodiments of the invention, the upper surface region 806 includes an inner circumferential edge 808 defining an aperture of the upper surface region through the patient table. In some embodiments of the invention, the aperture is adapted to receive a breast of the patient disposed therethrough. In other embodiments, including that illustrated in FIG. 7, the aperture is adapted to receive a subpanel 810 that traverses circumferential edge 808. The subpanel 810 is coupled to and/or supported by the patient table 804.

The subpanel 810 includes a subpanel surface region 812. A further inner circumferential edge 814 defines a subpanel aperture 816 through the subpanel. In the configuration illustrated, the subpanel aperture 816 is disposed coincident with a longitudinal centerline 818 of the patient table 804. In typical operation of the CBBCT imaging system, either breast of the patient may be disposed through the subpanel aperture 816 during imaging, with the patient being arranged on the upper surface 806 of the patient table 804 accordingly.

Although the inner circumferential edges 714, 724, 814 illustrated and discussed above are shown with substantially circular aspects, one of skill in the art will appreciate that the circumferential edge may be of any form considered advantageous according to the requirements of a particular application of the invention. Accordingly, in certain embodiments of the invention, the circumferential edge will be generally elliptical, or may be generally triangular, or of any other regular or irregular polygonal form, or of any arcuate form or any combination of arcuate and linear segments, or any combination of the foregoing, all of which are considered to be within the scope of the present disclosure.

Referring again to FIG. 7 the exemplary patient table 704 includes handles 730, 732. The handles 730, 732 are positioned and configured such that a patient is able to grasp the handles during mounting and operation of the ergonomic assist subsystem 702. This improves the ability of the patient to position the patient's body on the patient table 704, and provides stability to the patient during operation of the ergonomic assist system as it transitions from the fully elevated state to the fully descended state. In addition, grasping the handles will allow the patient to avoid movement during imaging, resulting in improved data/image quality.

In various embodiments of the invention, handles 730, 732 will be adjustable in one or more of the dimension of centerline 718, in transverse dimension 720, and in rotary fashion about a respective vertical axis disposed through the respective handle generally normal to surface 706 of the patient table 704. The reader will appreciate that the illustrated locations and configurations of the handles presented here are merely exemplary of many possible configurations. Other examples are provided below.

Figure 9A:
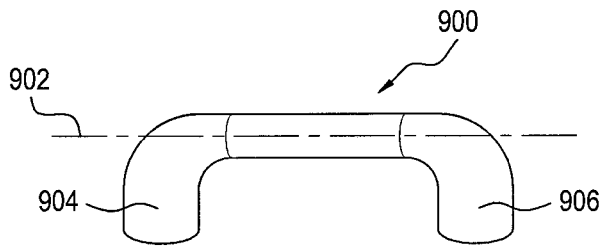
FIG. 9A shows, in schematic perspective view, certain features of a CBBCT imaging system prepared according to principles of the invention, including an exemplary handle thereof.

FIGS. 9A-9E show, in schematic perspective view, exemplary handles that will be employed in respective embodiments of the invention. One of skill in the art will readily appreciate the advantages of the particular handles shown, and of others that are suggested by the present disclosure, and are deemed to be within its scope. For example, FIG. 9A shows a handle 900 adapted to be grasped primarily about a transverse longitudinal axis 902 and to be substantially fixedly coupled to a patient table, directly or through an adjustment apparatus at first 904 and second 906 ends thereof. It will be noted that the handle of FIG. 9A bear some similarity to the handles shown as elements 730, 732 in FIG. 7.

Figure 9B:
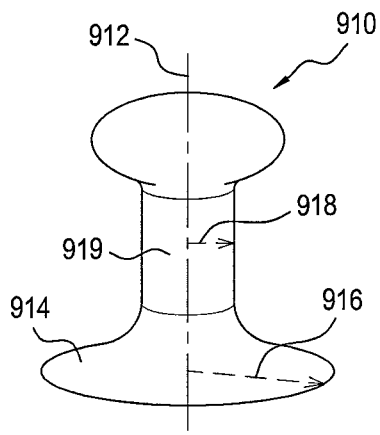
FIG. 9B shows, in schematic perspective view, additional features of a CBBCT imaging system prepared according to principles of the invention, including an exemplary handle thereof.

FIG. 9B shows an alternative handle 910 adapted to be grasped primarily about a longitudinal axis 912 disposed generally normal to a surface of the patient table. A flange portion 914 of the handle 910 has a generally larger radius 916, than a radius 918 of a grip portion 919. This extended flange provides for effective coupling to the table member, as well as improved stability and rigidity of the handle 910.

Figure 9C:
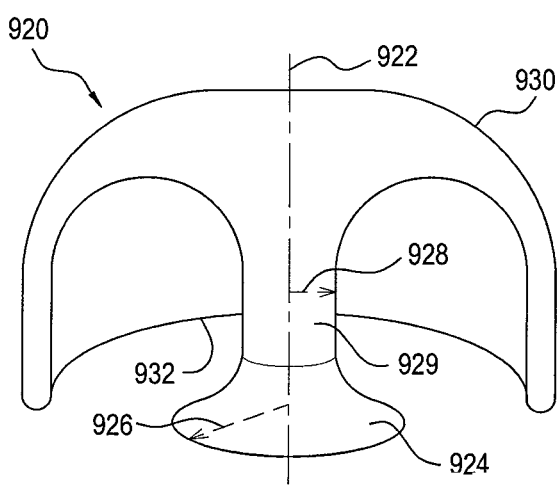
FIG. 9C shows, in schematic perspective view, still further features of a CBBCT imaging system prepared according to principles of the invention, including an exemplary handle thereof.

FIG. 9C shows a further alternative handle 920 adapted to be grasped primarily about a longitudinal axis 922 disposed generally normal to a surface of the patient table. A lower flange portion 924 of the handle 920 has a generally larger radius 926, than a radius 928 of a grip portion 929. An upper flange portion 930 is disposed in arcuate fashion away from the longitudinal axis 922, and downward towards the table member to which it couples at a lower edge 932 thereof. The extended lower and upper flanges provide for effective coupling of the handle 920 to the table member, as well as improved stability and rigidity of the handle.

Figure 9D:
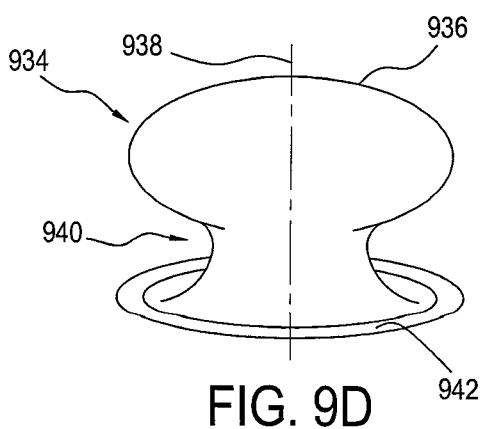
FIG. 9D shows, in schematic perspective view, yet other features of a CBBCT imaging system prepared according to principles of the invention, including an exemplary handle thereof.

FIG. 9D shows a further alternative handle 934 adapted to be grasped primarily about a bulbous upper surface 936 disposed generally parallel to a surface of the patient table and transverse to a longitudinal axis 938 of the handle 934. The longitudinal axis 938 is disposed generally normal to the surface of the patient table and, when in use, passes generally through the palm and/or the joints of the patient's hand. A circumferential recess 940 disposed below the bulbous upper surface 936 and generally transverse to longitudinal axis 938 is adapted to receive the tips of the patient's fingers therewithin, enhancing patient grip. A lower flange portion 942 of the handle 934 provides for effective coupling of the handle 934 to the table member, as well as improved stability and rigidity of the handle.

Figure 9E:
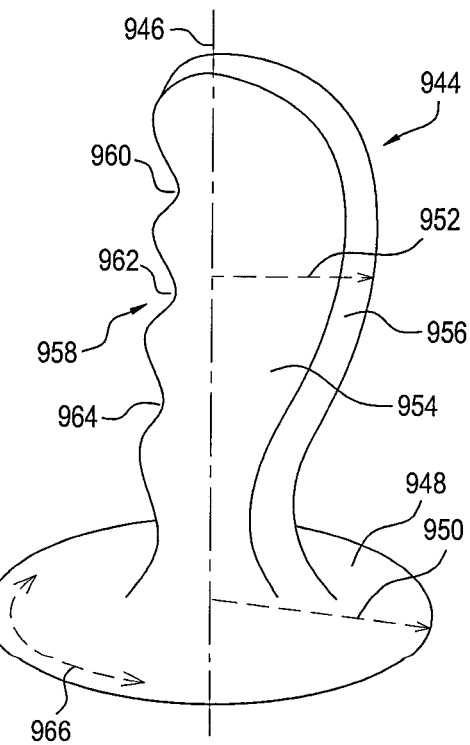
FIG. 9E shows, in schematic perspective view, still more aspects and features of a CBBCT imaging system prepared according to principles of the invention, including an exemplary handle thereof.

FIG. 9E shows a further alternative handle 944 adapted to be grasped primarily about a longitudinal axis 946 disposed generally normal to a surface of the patient table. A lower flange portion 948 of the handle 944 has a generally larger radius 950, than a lateral dimension 952 of a grip portion 954. One vertical surface region 956 of the handle 944 is generally convex and adapted to be placed in contact with a palm of a patient. The opposing vertical surface region 958 includes a plurality of concave recesses, e.g., 960, 962, 964, each adapted to receive a respective finger of the patient disposed therewithin. In certain embodiments, the handle 944 is substantially fixedly coupled to a table member of the patient table. In other embodiments, the handle is coupled to the table member through a rotary bearing and adapted to pivot circumferentially 966 substantially freely, or to be adjusted by pivoting circumferentially 966 and then releasably fixed in place, according to the requirements of a particular application of the invention. This pivotal motion allows adjustment of the position of surfaces 956 and 958 for optimum comfort of a patient grasping the handle.

In the context of the foregoing discussions, FIGS. 10A-10F show, in schematic fashion, a variety of exemplary subpanel configurations that fall within the scope of the present invention and are similar to subpanels 710 and 810 described above in relation to FIGS. 7 and 8.

FIGS. 10A-10C show respectively, in schematic proximal elevation, exemplary subpanels having a variety of aperture locations and sizes.

Referring first to FIG. 10A, subpanel 1000 includes a subpanel surface region 1002. An inner circumferential edge 1004 defines a subpanel aperture 1006 through the subpanel. Consistent with the discussion above, the aperture 1006 is adapted to receive a patient breast to be imaged therethrough. In the configuration illustrated, the subpanel aperture 1006 is disposed to the left of a longitudinal centerline 1008 of the subpanel 1000. Accordingly, in typical operation of the CBBCT imaging system, a left breast of the patient will be disposed through the subpanel aperture 1006 during imaging.

FIG. 10B shows a subpanel 1012 similar to subpanel 1000. As with subpanel 1000, subpanel 1012 has an inner circumferential edge 1014 that defines a subpanel aperture 1016 through the subpanel 1012. Like aperture 1006, aperture 1016 is disposed to the left of a longitudinal centerline 1018 of the subpanel 1012. However, aperture 1006 has a diameter of 1020 that is relatively smaller than the corresponding diameter 1022 of aperture 1016.

FIG. 10C shows a subpanel 1026 similar to subpanels 1000 and 1012. As with subpanel 1000, subpanel 1026 has an inner circumferential edge 1028 that defines a subpanel aperture 1030 through the subpanel 1026. Aperture 1030 has a diameter of 1032 that is substantially equal to corresponding diameter 1022 of aperture 1016. However, a centroid of aperture 1030 is disposed substantially coincident with centerline 1034 of the subpanel 1026. Accordingly, whereas apertures 1006 and 1016 are primarily configured for receiving a left breast of the patient for imaging, aperture 1030 is well adapted to receiving either a left breast or a right breast.

It will also be appreciated by one of skill in the art that, where appropriate perimeter configurations and coupling features are provided, symmetries of the illustrated panels will be used in respective embodiments of the invention to image, for example, either a left breast or a right breast by symmetric rotation of subpanel 1000 or 1012 about centerlines 1008 and 1018 respectively.

Likewise, rotation of the panels about an axis transverse to the respective centerlines can be used to locate the illustrated apertures relatively higher or lower respectively, according to the needs of a taller or shorter patient.

In light of the foregoing discussion, it will be appreciated by the reader that, in certain embodiments of the invention, a plurality of subpanels will be provided along with an imaging system, such that the subpanel with the appropriate aperture will be selected according to the height, weight, breast size and other parameters of the patient.

In another aspect or embodiment of the invention, individual reusable subpanels will be purchased so as to be available where required. In still other embodiments of the invention, disposable subpanels will be employed for single use with a respective patient, and thereafter discarded.

FIGS. 10D-10F show schematic representations of a further subpanel 1050 prepared according to principles of the invention. Subpanel 1050 is shown in cutaway view, and illustrates an adjustment mechanism 1052 included in subpanel 1050.

In the exemplary embodiment illustrated, adjustment mechanism 1052 includes an adjustable mechanical iris mechanism 1054. The adjustable iris mechanism 1054 includes a plurality of leaf elements, e.g., 1056, 1058 respectively coupled to corresponding operative links 1060, 1062. One of skill in the art will recognize the adjustable iris mechanism 1054 as similar in form and function to iris mechanisms employed in photographic cameras. Accordingly, by operation of the operative links 1060, 1062, the leaf elements 1056, 1058 will be urged to pivot so as to adjust a diameter of an aperture 1064 to a preferred value according to the requirements for imaging a particular patient breast.

By way of further illustration, in FIG. 10E exemplary iris mechanism 1070 is adjusted and configured to present an aperture 1072 having a relatively small diameter 1074. In FIG. 10F, exemplary iris mechanism 1070 is adjusted and configured to present the same aperture 1072 with a relatively large diameter 1076.

Figure 11:
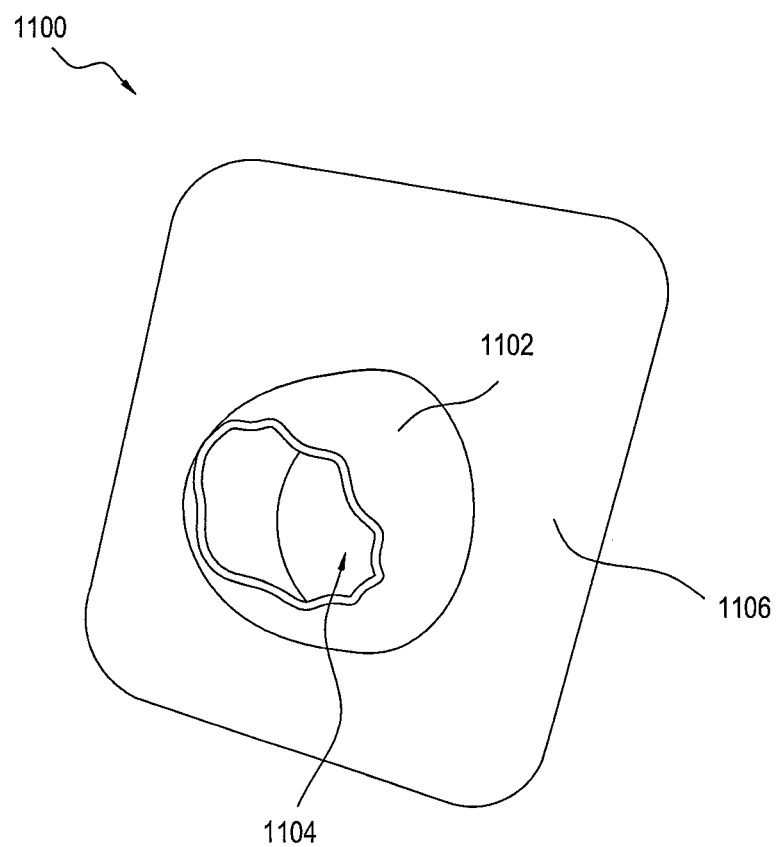
FIG. 11 shows, in schematic perspective view, certain further features of a CBBCT imaging system prepared according to principles of the invention, including exemplary breast stabilization features.

In a still further aspect of the invention FIG. 11 shows, in schematic distal cutaway perspective view, a subpanel 1100 including a breast stabilizer unit 1102 adapted and configured to support and stabilize a patient breast during imaging. As illustrated, the breast stabilizer unit 1102 is coupled to the subpanel 1100 at aperture 1104 of distal surface region 1106.

One of skill in the art will readily appreciate the various benefits and modalities for employing a breast stabilizer unit like the exemplary stabilizer unit presented herewith upon review of the related applications listed above.

Figure 12:
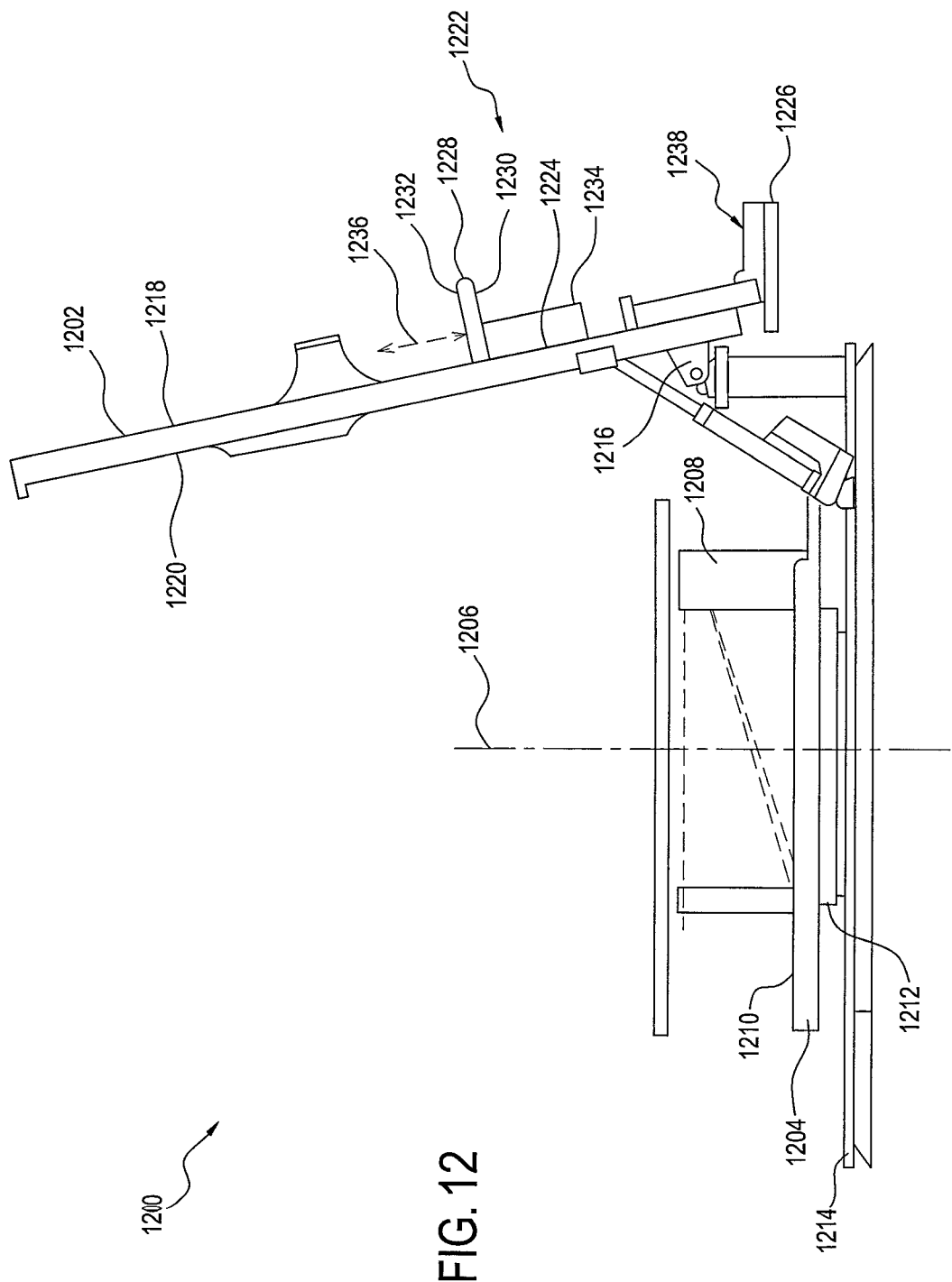
FIG. 12 shows, in schematic side elevation, additional aspects and features of an exemplary CBBCT imaging system, including a patient saddle prepared according to principles of the invention.

FIG. 12 shows, in schematic side elevation, a portion of an exemplary CBBCT imaging system 1200, similar to system 200, including a pivotable patient interface panel 1202. The CBBCT imaging system 1200 includes a CBBCT gantry 1204 configured to rotate about, e.g., a generally vertical axis of rotation 1206.

Like systems 100 and 200 described above, system 1200 includes an x-ray source 1208. The exemplary x-ray source 1208 is mounted on, and supported by, a mounting surface 1210 of the CBBCT gantry 1204. The CBBCT gantry 1204 is supported by a bearing 1212, and arranged for rotation about the axis of rotation 1206. The bearing 1212 is, in turn, coupled to and supported by a base member (or foundation element) 1214. The patient interface panel 1202 is pivotally coupled to the base member 1214 at a hinge element 1216.

The patient interface panel 1202 has a first patient interface surface region 1218 and a second distal surface region 1220, where the distal surface region 1220 is disposed in spaced relation to the patient interface surface region 1218. The exemplary patient interface panel 1202 is similar in form and function to the patient interface panel 238 of FIG. 2.

In a manner similar to that described above, the patient interface surface region 1218 is arranged to segregate the patient from the balance of the CBBCT gantry 1204 and the moving equipment coupled to it. In the illustrated embodiment, an exemplary seat apparatus 1222 is coupled to, and supported by, a corresponding portion 1224 of the patient interface surface region 1218. In other embodiments of the invention, the exemplary seat apparatus 1222 is coupled to and supported by the base member 1214, and/or a patient step 1226, or to any other location, feature or aspect of the CBBCT imaging system, or combination of the same, appropriate to the requirements of a particular application and embodiment of the invention.

The seat apparatus 1222 includes a saddle portion 1228 with a structural body member 1230 and a saddle upper surface region 1232. Saddle upper surface region 1232 is adapted to position and support a patient sitting astride the saddle portion 1228 during imaging as well as during optional supplemental procedures.

In the illustrated embodiment, structural body member 1230 is substantially fixedly coupled to an upper end of an exemplary seat column 1234 which is coupled to the CBBCT imaging system 1200 as described above, directly or through an appropriate positional adjustment apparatus. The seat column is optional, and in certain embodiments of the invention, the saddle structural body member is coupled directly to the CBBCT imaging system 1200.

Accordingly, in certain embodiments of the invention, a lower end of the exemplary seat column 1234 is operatively coupled to a seat adjustment mechanism. The seat adjustment a mechanism is coupled, directly or indirectly, to the patient interface panel 1202 for support. Consequently, the weight of a patient seated on the saddle upper surface region 1232 is transferred through the structural body member 1230 of the saddle to the seat column 1234, and from there through the seat adjustment mechanism to the patient interface panel 1202.

In a desirable aspect of certain embodiments of the invention, the seat adjustment mechanism permits positional adjustment of the saddle portion 1228 vertically 1236 i.e., transverse to an upper surface 1238 of the patient step 1226. In certain embodiments, the seat adjustment mechanism also permits pivotal rotations i.e., yaw of the saddle about a longitudinal axis of the seat column 1234 and pitch about a transverse axis.

Beyond this, in certain embodiments of the invention, roll of the saddle portion 1228 will also be adjustable to ensure comfort and optimal positioning of the patient with respect to the pivotable patient interface panel 1202.

In a still further aspect of the invention, in certain embodiments the saddle will be removable or foldable, or otherwise displaceable so that a patient being imaged will not sit on the saddle, but will stand on an upper surface 1238 of the step portion 1226, for example. Accordingly, seating on the saddle will be available where desirable, but the saddle need not be employed where a standing mode of patient support is preferable.

As will be appreciated by one of skill in the art, the structural body member 1230 and saddle upper surface region 1232 will be shaped and configured to promote optimal comfort and positioning of the patient with respect to the pivotable patient interface panel 1202. In certain embodiments, the saddle portion 1228 will include materials that advantageously are biocompatible and exhibit desirable characteristics of rheology and elastic durometer.

Accordingly, in respective embodiments of the invention, the saddle will include materials appropriate to achieve these ends. A variety of exemplary materials corresponding to respective embodiments of the invention are provided below in relation to the description accompanying FIGS. 13A and 13B below.

Figure 13A:
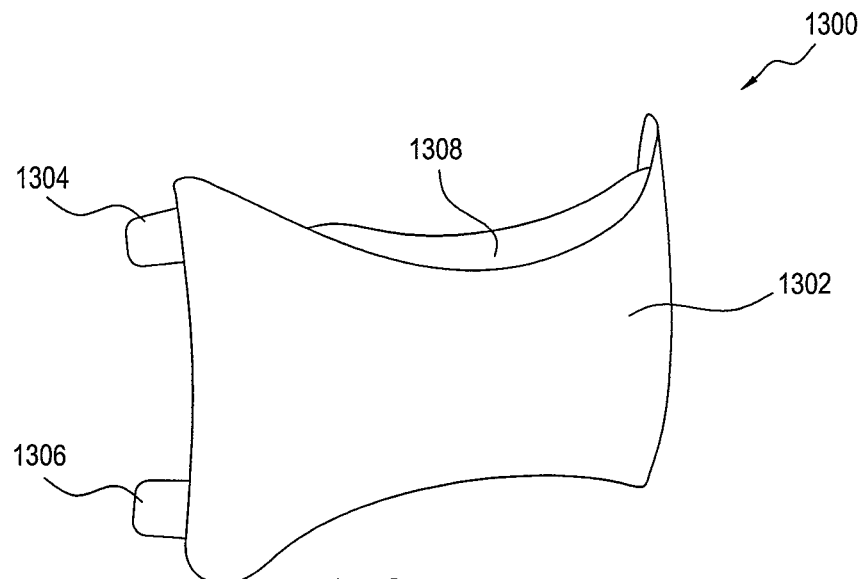
FIG. 13A shows, in elevated schematic perspective view, certain aspects of an exemplary CBBCT imaging system, including certain safety features thereof prepared according to principles of the invention.
Figure 13B:
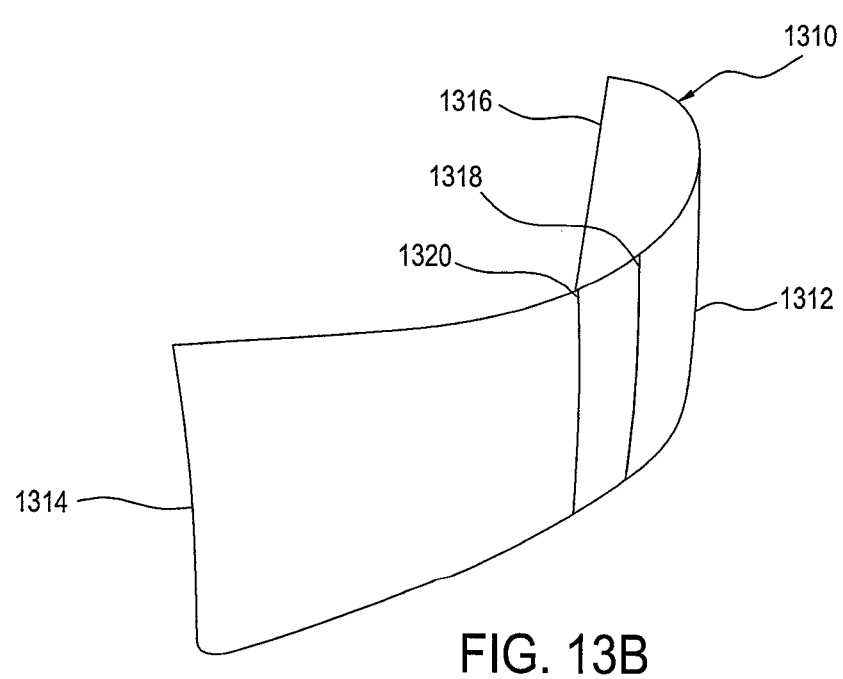
FIG. 13B shows, in elevated schematic perspective view, certain aspects of an exemplary CBBCT imaging system, including additional safety features thereof prepared according to principles of the invention.

FIGS. 13A and 13B show, in schematic perspective view, safety elements exemplary of safety feature 424 of CBBCT imaging system 400. Referring again to FIG. 7, exemplary safety elements will include a safety belt 734 and buckle 736.

FIG. 13A shows a safety belt 1300 for a CBBCT imaging system. Safety belt 1300 includes a generally flexible member 1302. In the illustrated embodiment, flexible member 1302 includes, for example, a textile material such as, for example, a woven textile material, a knitted textile material, a felted textile material, or a chain-linked textile material. In other embodiments of the invention, the flexible member 1302 includes one or more of a molded elastomeric polymer, a spray-formed elastomeric polymer a rope or cable, a natural material such as a natural polymer, a leather, a vegetable material, or other material or combination of materials appropriate to the objectives and functions described herewith.

The illustrated safety belt 1300 includes a coupling mechanism e.g., 1304, 1306 adapted for detachably coupling the safety belt 1300 to a patient interface panel such as e.g., 704 of FIG. 7. In various embodiments of the invention, the coupling mechanism, e.g., 1304, 1306 will include one or more of a buckle, a button, a hook and loop fastener, a mechanical snap fastener, a magnet fastener, an adhesive fastener, or any other fastener appropriate to the purposes in light of the present disclosure that is known or becomes known in the art, as well as combinations of the same.

In certain embodiments of the invention, the safety belt 1300 will include a cushion element 1308. In certain embodiments, the cushion element will include a generally elastic element that serves to distribute forces across an inner surface of the flexible element 1302, operative to avoid excessive pressure at points of contact with the patient's back.

In certain embodiments of the invention, the cushion element 1308 will include an expanding element such as for example, an air bladder, a liquid bladder, or a mechanical actuator. In certain embodiments of the invention, the expanding element is adapted to expand in a controlled fashion once the safety belt is coupled to the patient interface panel, thereby urging the patient against the patient interface surface.

FIG. 13B shows an alternative safety belt 1310 for a CBBCT imaging system. Like safety belt 1300, safety belt 1310 includes a generally flexible member 1312. In the illustrated embodiment, flexible member 1312 includes, for example, a textile material and/or any of the materials provided as examples above.

The flexible member 1312 has a first end 1314 and a second end 1316 that are adapted to be coupled to respective regions of a patient interface panel. In certain embodiments of the invention, the respective ends 1314 and 1316 are substantially permanently coupled to the patient interface panel. In other embodiments of the invention, ends 1314 and 1316 are removably and/or adjustably coupled to the patient interface panel.

In the illustrated embodiment, the flexible member 1312 has third 1318 and fourth 1320 internal ends that are adapted to be releasably coupled to each other. Accordingly, internal ends 1318, 1320 will include respective complementary coupling features. Thus, for example, internal ends 1318, 1320 will include respective complementary portions of a buckle, a button, a hook and loop fastener, a mechanical snap fastener, a magnet fastener, or any other fastener appropriate to the purposes in light of the present disclosure that is known or becomes known in the art, as well as combinations of the same.

In some embodiment of the invention, the safety belt 1300, 1310, including elements of its assembly, will include one or more of polyethylene, polypropylene, polybutylene, polystyrene, polyester, acrylic polymers, polyvinylchloride, polyamide, or polyetherimide like ULTEM®; a polymeric alloy such as Xenoy® resin, which is a composite of polycarbonate and polybutyleneterephthalate or Lexan® plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, polyesterimide anhydrides with terminal anhydride group or lateral anhydrides.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used.

A CBBCT scanning system includes a base member and a CBBCT gantry subsystem, where the CBBCT gantry subsystem is coupled to and supported by the base member. The CBBCT gantry subsystem includes a CBBCT gantry that is adapted and configured to rotate about an axis of rotation; and a patient interface panel.

The patient interface panel has a patient interface surface with an elevation axis. The patient interface panel is pivotally coupled to the base member with a pivotal hinge. The patient interface panel is adapted to pivot about the pivotal hinge. The patient interface panel pivots between a first patient loading configuration with an elevation axis that is disposed generally aligned with the axis of rotation and a second patient imaging configuration with an elevation axis that is disposed generally transverse to the axis of rotation.

In certain embodiments, a CBBCT scanning system includes an actuator. The actuator is coupled between the base member and the patient interface panel. The actuator is adapted to motivate the pivot about the pivotal hinge between the first patient loading configuration and the second patient imaging configuration.

In certain embodiments, the CBBCT scanning system includes an actuator that is a linear actuator. In certain embodiments, the CBBCT scanning system includes an actuator that is a rotary actuator.

In certain embodiments, the CBBCT scanning system includes a patient interface panel with a patient interface surface region that has an aperture through it. In some embodiments, a patient interface subpanel is disposed within the aperture.

In certain embodiments, the CBBCT scanning system includes a patient interface subpanel with a breast aperture. The breast aperture is adapted to receive a patient breast therethrough for imaging.

In certain embodiments, the CBBCT scanning system includes a patient interface subpanel that has a breast stabilization unit. The breast stabilization unit is adapted to support the patient breast during imaging.

In certain embodiments, the CBBCT scanning system includes a patient interface panel with a patient support step assembly. In some embodiments, the step assembly is coupled to a seat adjustment mechanism.

In certain embodiments, the CBBCT scanning system includes a seat adjustment mechanism that is adapted to adjust a saddle upper surface of a saddle portion in a vertical degree of freedom. The seat adjustment mechanism is adapted to adjust a saddle upper surface of a saddle portion in a horizontal degree of freedom.

The method of conducting a CBBCT scan includes providing a base member and a CBBCT gantry. The CBBCT gantry is rotationally coupled to the base member for rotation about an axis of rotation. The axis of rotation is substantially immobile with respect to the base member. Also provided is a patient interface panel that is pivotally coupled to the base member. The patient interface panel is disposed in a generally upright orientation. The patient is then introduced to the patient interface panel. Thereafter, the patient interface panel is disposed in a second scanning orientation. Thereafter, the CBBCT gantry is operated to conduct the CBBCT scan, and thereafter, the patient interface panel is disposed back in the first generally upright orientation.

In certain embodiments, the method of conducting a CBBCT scan is further comprised of providing a patient step that has an upper surface region that is adapted to support the patient during imaging and adjusting the patient step for patient positioning.

In certain embodiments, the first generally upright orientation includes an orientation between at least about 80° and at least 90° with respect to the horizontal.

In certain embodiments, the first generally upright orientation includes an orientation between at least about 70° and at least 80° with respect to the horizontal whereas in some embodiments the first generally upright orientation comprises an orientation between at least about 50° and at least 70° with respect to the horizontal.

In certain embodiments, the method of conducting a CBBCT scan includes a second scanning orientation comprising an orientation between at least about 0° and at least 20° with respect to the horizontal.

In some embodiments, the second scanning orientation comprises an orientation between at least about 20° and at least 45° with respect to the horizontal while in certain embodiments the second scanning orientation comprises an orientation between at least about 45° and at least 70° with respect to the horizontal.

In certain embodiments, the method of conducting a CBBCT scan includes coupling a patient interface subpanel to the patient interface panel while in some embodiments the method of conducting a CBBCT scan includes coupling the patient to the patient interface panel with a safety device.

In certain embodiments, the method of conducting a CBBCT activating the safety device and urging the patient towards the patient interface panel with the safety device.

In certain embodiments, the method of conducting a CBBCT scan includes coupling a breast stabilization unit to the patient interface subpanel.

In certain embodiments, the method of conducting a CBBCT scan includes ascertaining a patient parameter and selecting the breast stabilization unit according to the patient parameter.

In certain embodiments, the method of conducting a CBBCT scan includes coupling a handle to the patient interface panel.

While the exemplary embodiments described above have been chosen primarily from the field of apparatus, and corresponding systems and methods in the operation of a CBBCT imaging system, including ergonomically improved systems and methods thereof, one of skill in the art will appreciate that the principles of the invention are equally well applied, and that the benefits of the present invention are equally well realized in a wide variety of other imaging technologies, for example, imaging of other body parts and imaging of other subjects such as industrial and technological products. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A CBBCT scanning system comprising:
 a base member;
 a CBBCT gantry subsystem coupled to and supported by said base member, said CBBCT gantry subsystem including a CBBCT gantry, said CBBCT gantry being adapted and configured to rotate about an axis of rotation; and
 a patient interface panel, said patient interface panel including a patient support step assembly, said patient interface panel having a patient interface surface, said patient interface surface having an elevation axis, said patient interface panel being pivotally coupled to said base member with a pivotal hinge, said patient interface panel being adapted to pivot about said pivotal hinge between a first patient loading configuration in which said elevation axis is disposed generally aligned with said axis of rotation to support said patient in a standing configuration, and a second patient imaging configuration in which said elevation axis is disposed generally transverse to said axis of rotation to support said patient in a prone configuration.

2. A CBBCT scanning system as defined in claim 1 further comprising an actuator, said actuator being coupled between said base member and said patient interface panel, said actuator being adapted to motivate said pivot about said pivotal hinge between said first patient loading configuration and said second patient imaging configuration.

3. A CBBCT scanning system as defined in claim 2 wherein said actuator comprises a linear actuator.

4. A CBBCT scanning system as defined in claim 2 wherein said actuator comprises a rotary actuator.

5. A CBBCT scanning system as defined in claim 1 wherein said patient interface panel includes a patient interface surface region with an aperture therethrough.

6. A CBBCT scanning system as defined in claim 5 further comprising a patient interface subpanel disposed within said aperture.

7. A CBBCT scanning system as defined in claim 6 wherein said patient interface subpanel includes a breast aperture, said breast aperture being adapted to receive a patient breast therethrough for imaging.

8. A CBBCT scanning system as defined in claim 6 wherein said patient interface subpanel includes a breast stabilization unit, said breast stabilization unit being adapted to support said patient breast during imaging.

9. A CBBCT scanning system as defined in claim 1 wherein said step assembly is coupled to a seat adjustment mechanism.

10. A CBBCT scanning system as defined in claim 9 wherein said seat adjustment mechanism is adapted to adjust a saddle upper surface of a saddle portion in a vertical degree of freedom.

11. A CBBCT scanning system as defined in claim 9 wherein said seat adjustment mechanism is adapted to adjust a saddle upper surface of a saddle portion in a horizontal degree of freedom.

12. A method of conducting a CBBCT scan comprising:
 providing a base member;
 providing a CBBCT gantry, said CBBCT gantry being rotationally coupled to said base member for rotation about an axis of rotation, said axis of rotation being substantially immobile with respect to said base member;
 providing a patient interface panel;
 pivotally coupling said patient interface panel to said base member;
 disposing said patient interface panel in a first generally upright orientation;
 introducing a patient to said patient interface panel;
 thereafter, disposing said patient interface panel in a second scanning orientation;
 thereafter, operating said CBBCT gantry to conduct said CBBCT scan; and
 thereafter, disposing said patient interface panel in said first generally upright orientation.

13. A method of conducting a CBBCT scan as defined in claim 12, further comprising:
 providing a patient step, said patient step having a patient step upper surface region, said patient step upper surface region being adapted to support said patient during imaging; and
 adjusting said patient step for patient positioning.

14. A method of conducting a CBBCT scan as defined in claim 12 wherein said first generally upright orientation comprises an orientation between at least about 80° and at least 90° with respect to the horizontal.

15. A method of conducting a CBBCT scan as defined in claim 12 wherein said first generally upright orientation comprises an orientation between at least about 70° and at least 80° with respect to the horizontal.

16. A method of conducting a CBBCT scan as defined in claim 12 wherein said first generally upright orientation comprises an orientation between at least about 50° and at least 70° with respect to the horizontal.

17. A method of conducting a CBBCT scan as defined in claim 12 wherein said second scanning orientation comprises an orientation between at least about 0° and at least 20° with respect to the horizontal.

18. A method of conducting a CBBCT scan as defined in claim 12 wherein said second scanning orientation comprises an orientation between at least about 20° and at least 45° with respect to the horizontal.

19. A method of conducting a CBBCT scan as defined in claim 12 wherein said second scanning orientation comprises an orientation between at least about 45° and at least 70° with respect to the horizontal.

20. A CBBCT scanning system comprising:
 a base member;
 a CBBCT gantry subsystem coupled to and supported by said base member, said CBBCT gantry subsystem including a CBBCT gantry, said CBBCT gantry being adapted and configured to rotate about an axis of rotation; and
 a patient interface panel, said patient interface panel having a patient interface surface with an aperture therethrough and a patient interface subpanel disposed within said aperture, said patient interface subpanel including a breast aperture of variable size, said patient interface surface having an elevation axis, said patient interface panel being pivotally coupled to said base member with a pivotal hinge, said patient interface panel being adapted to pivot about said pivotal hinge between a first patient loading configuration in which said elevation axis is disposed generally aligned with said axis of rotation and a second patient imaging configuration in which said elevation axis is disposed generally transverse to said axis of rotation.

21. A CBBCT scanning system as defined in claim 20 wherein said patient interface subpanel including a breast aperture of variable size comprises:
   a replaceable panel having a breast aperture of fixed size therewithin.

22. A CBBCT scanning system as defined in claim 20 wherein said patient interface subpanel including a breast aperture of variable size comprises:
   a replaceable panel having a breast aperture of adjustable size therewithin.

23. A CBBCT scanning system as defined in claim 20 wherein said breast aperture is placed asymmetrically with respect to a centerline of said patient interface subpanel.

* * * * *